United States Patent
Wang et al.

(10) Patent No.: US 10,688,086 B2
(45) Date of Patent: Jun. 23, 2020

(54) METHOD FOR TREATING CANCER WITH DIHYDROPYRIDINE CALCIUM ANTAGONIST

(71) Applicant: GERMARK BIOTECHNOLOGY CO., LTD, Taichung (TW)

(72) Inventors: Prince Wang, Taichung (TW); Chang Bi Wang, Taichung (TW)

(73) Assignee: GERMARK BIOTECHNOLOGY CO., LTD, Taichung (TW)

( * ) Notice: Subject to any disclaimer, the term of this patent is extended or adjusted under 35 U.S.C. 154(b) by 0 days.

(21) Appl. No.: 16/343,687

(22) PCT Filed: Oct. 19, 2016

(86) PCT No.: PCT/CN2016/102550
§ 371 (c)(1),
(2) Date: Apr. 19, 2019

(87) PCT Pub. No.: WO2018/072135
PCT Pub. Date: Apr. 26, 2018

(65) Prior Publication Data
US 2019/0240207 A1    Aug. 8, 2019

(51) Int. Cl.
*A61K 31/4422* (2006.01)
*A61P 35/04* (2006.01)
*A61P 35/00* (2006.01)

(52) U.S. Cl.
CPC .......... *A61K 31/4422* (2013.01); *A61P 35/00* (2018.01); *A61P 35/04* (2018.01)

(58) Field of Classification Search
CPC .................................................... A61K 31/435
See application file for complete search history.

(56) References Cited

FOREIGN PATENT DOCUMENTS

CN    101569624 A    11/2009
TW    201615191 A    5/2016

OTHER PUBLICATIONS

Machine Translation of CN101569624.*

* cited by examiner

*Primary Examiner* — San Ming R Hui
(74) *Attorney, Agent, or Firm* — Muncy, Geissler, Olds & Lowe, P.C.

(57) ABSTRACT

The present invention discloses a method for treating a cancer with a dihydropyridine calcium antagonist, which comprises administering, to a cancer patient, a dihydropyridine calcium antagonist in an amount effective in inhibiting the cancer metastasis and reducing the proliferation of cancer cells, so as to achieve the effect of increasing the survival rate of patients with cancers.

5 Claims, 39 Drawing Sheets

METHOD FOR TREATING CANCER WITH DIHYDROPYRIDINE CALCIUM ANTAGONIST

BACKGROUND OF THE INVENTION

1. Field of the Invention

The present invention relates to a second use of a compound, in particular to a method for treating a cancer with a dihydropyridine calcium antagonist.

2. Description of the Related Art

Liver cancer is one of the most common cancers of the gastrointestinal tract in the world. However, since the hepatic nerves are mostly distributed on the liver surface, no symptoms are exhibited in the early stage of liver cancer, and there are no obvious symptoms even when the liver cancer metastasizes. Therefore, the liver cancer is mostly diagnosed at the end stage. Currently, Sorafenib is often clinically used as a targeting therapeutic drug, which is an oral multi-kinase inhibitor and results in apoptosis mainly by inhibiting angiogenesis and Raf kinase/MAPK pathway. However, recent studies have pointed out that the therapeutic effect of administering Sorafenib to patients with advanced liver cancers is not good, and drug resistance may be developed.

Amlodipine is a dihydropyridine calcium antagonist useful in the treatment of high blood pressure or the prevention of angina. Further, the main mechanism of action of Amlodipine is to block calcium ions from entering the heart and vascular smooth muscle cells, to achieve the purpose of lowering blood pressure by reducing the vasoconstriction, and indirectly relaxing and dilating the blood vessels to allow more blood to flow in the blood vessels.

SUMMARY OF THE INVENTION

The present invention mainly aims at providing a second use of a compound, in particular to a method for treating a cancer with a dihydropyridine calcium antagonist. Numerous dihydropyridine calcium antagonists are currently used in clinical practice, including, but not limited to, Nifedipine, sustained-release Nifedipine, Felodipine, Lacidipine, Amlodipine, and Cilnidipine.

For example, Amlodipine has a chemical formula below:

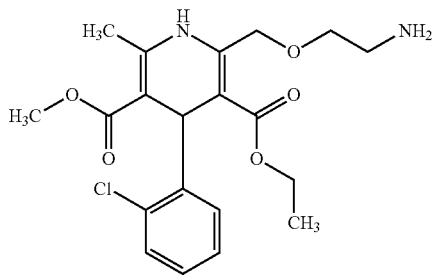 [SMILES: CCOC(=O)C1=C(COCCN)NC(C)=C(C(=O)OC)C1c1ccccc1Cl]

Therefore, in order to achieve the above object, an embodiment of the present invention discloses a method for treating a cancer with a dihydropyridine calcium antagonist, comprising administering an effective amount of a dihydropyridine calcium antagonist to a cancer patient, where the dihydropyridine calcium antagonist is used at a dosage of 100 mg/90 day or more.

By administering an effective amount of a dihydropyridine calcium antagonist to a cancer patient, the cancer metastasis can be effectively inhibited and the cancer cell proliferation can be reduced to achieve the effect of improving the survival rate of the cancer patient.

In one embodiment of the present invention, the dihydropyridine calcium antagonist is Amlodipine, which is administered at a dosage of at least 100 mg/90 days or 120 mg/30 days. For example, if a dose of 5 mg/day is employed in clinic, the administration of Amlodipine is continued for at least 20 days; or on average, at least 1 mg of Amlodipine needs to be administered per day.

Preferably, the cancer is gastric cancer, liver cancer, lung cancer, breast cancer, colorectal cancer, pancreatic cancer, bladder cancer, or cervical cancer.

In another embodiment of the present invention, the cancer patient suffers from advanced cancer and the dihydropyridine calcium antagonist is administered to the cancer patient to inhibit the cancer metastasis, where the advanced cancer includes cancers of stages III and IV.

DETAILED DESCRIPTION OF THE PREFERRED EMBODIMENTS

Figure 1:
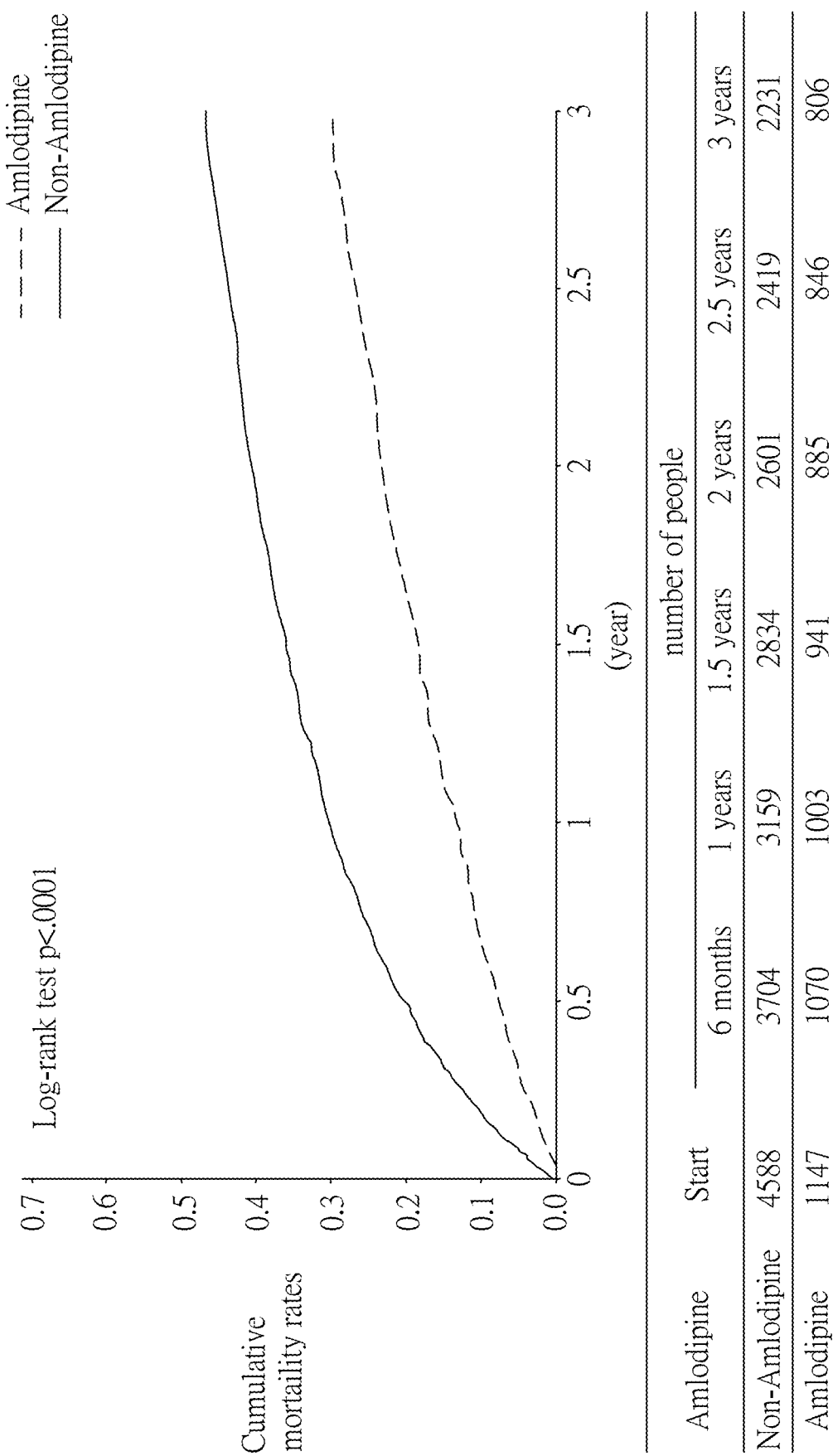
FIG. 1 shows the result of statistical analysis at various times after patients having gastric cancer receive or receive no treatment with Amlodipine.
Figure 2:
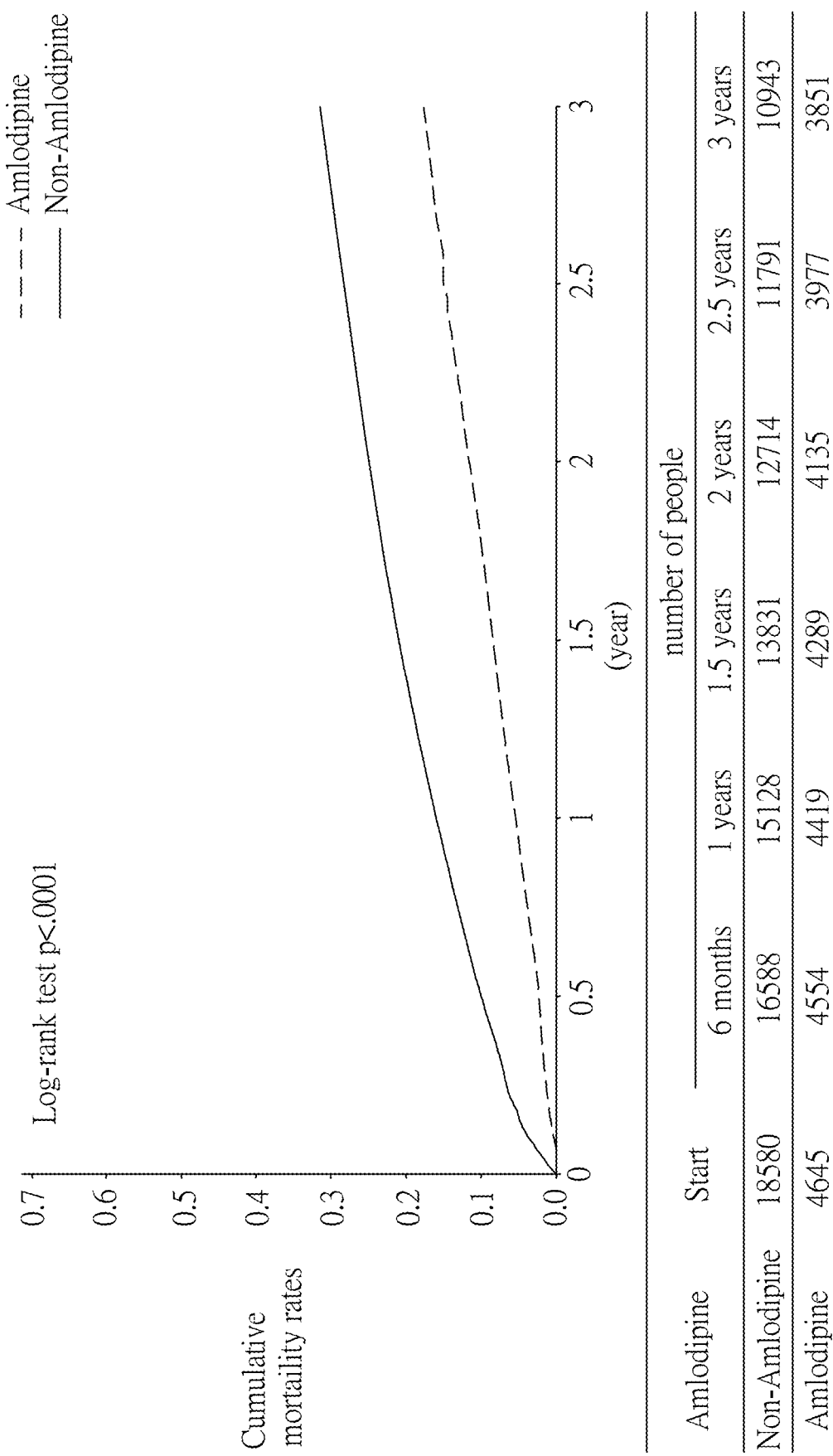
FIG. 2 shows the result of statistical analysis at various times after patients having colorectal cancer receive or receive no treatment with Amlodipine.
Figure 3:
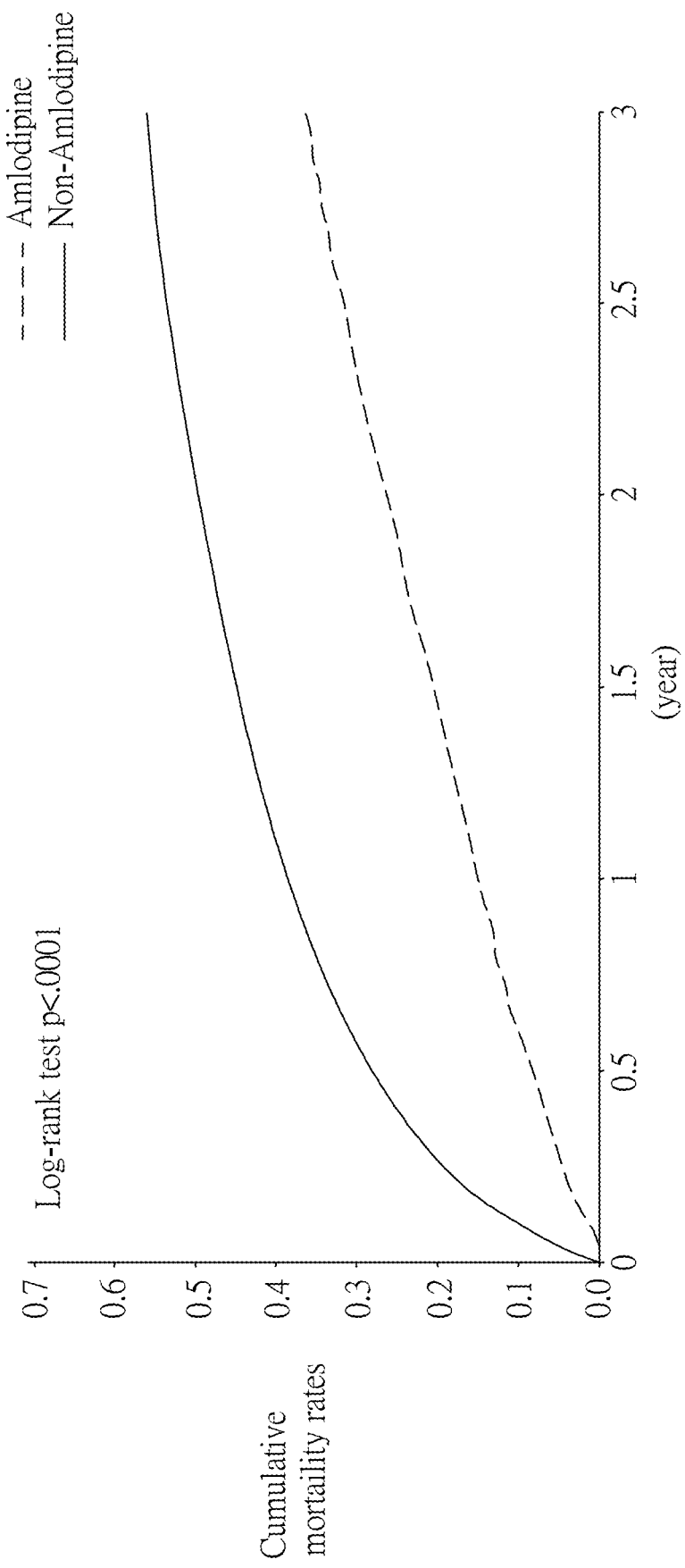
FIG. 3 shows the result of statistical analysis at various times after patients having liver cancer receive or receive no treatment with Amlodipine.
Figure 4:
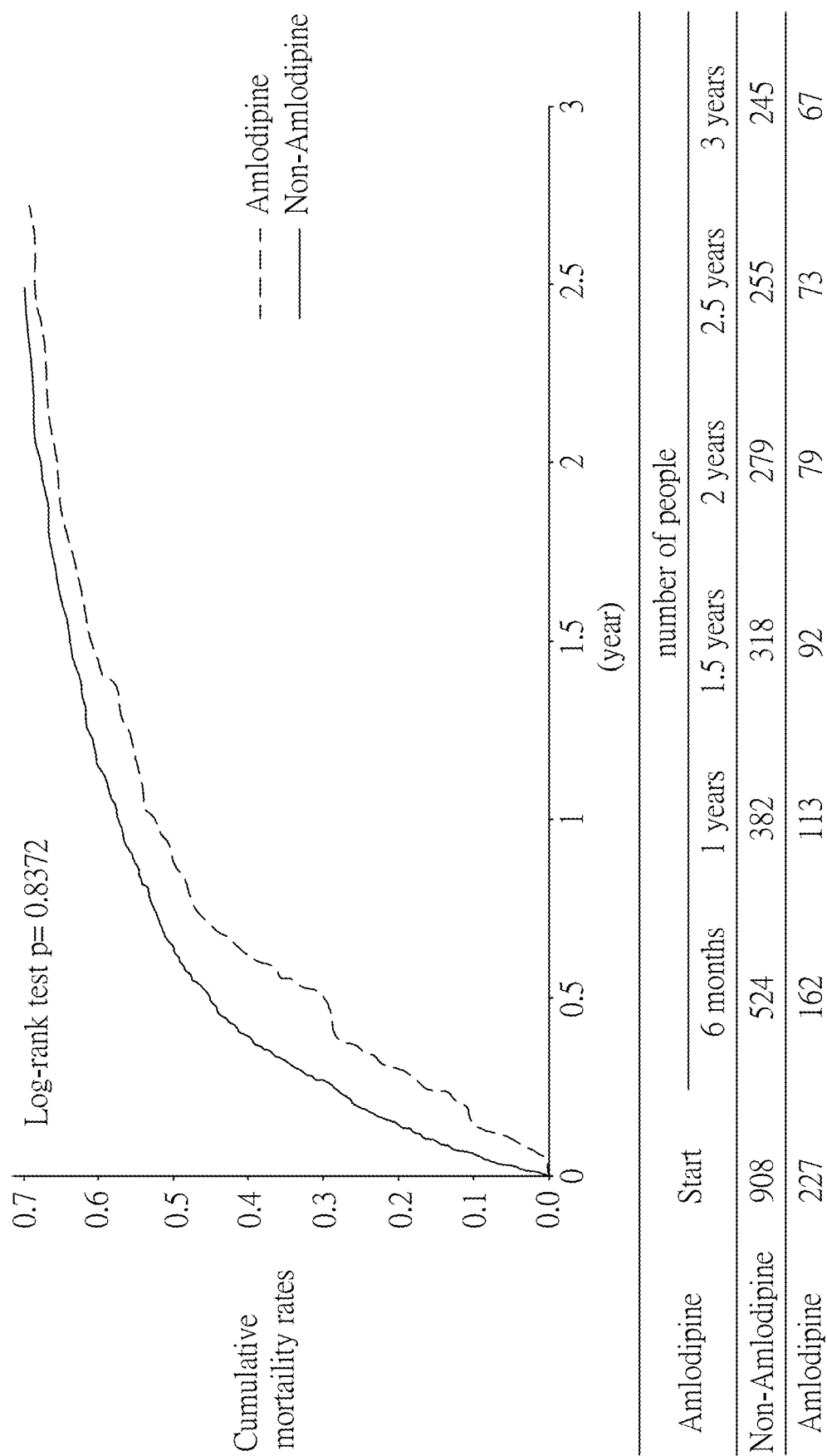
FIG. 4 shows the result of statistical analysis at various times after patients having pancreatic cancer receive or receive no treatment with Amlodipine.
Figure 5:
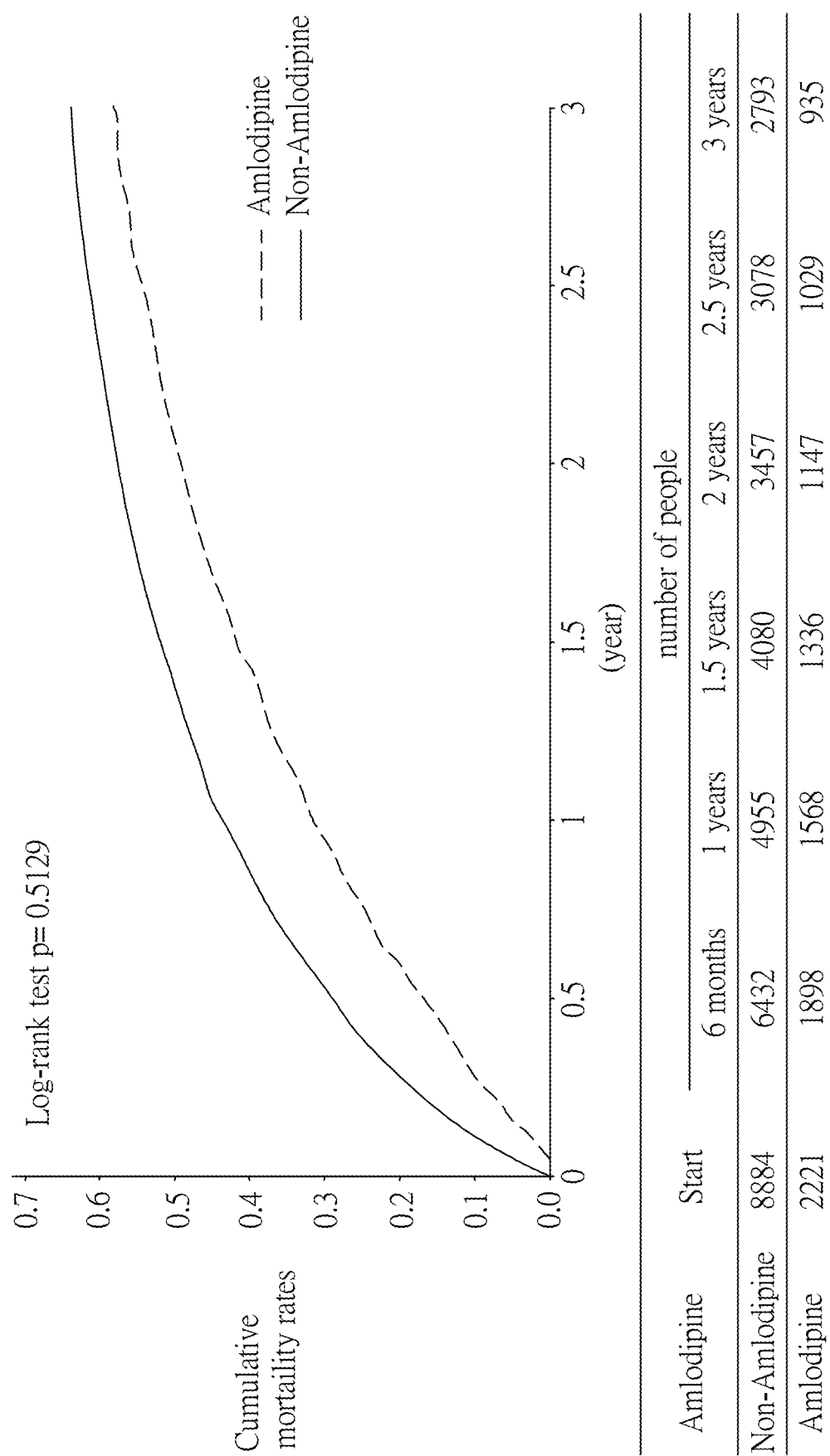
FIG. 5 shows the result of statistical analysis at various times after patients having lung cancer receive or receive no treatment with Amlodipine.
Figure 6:
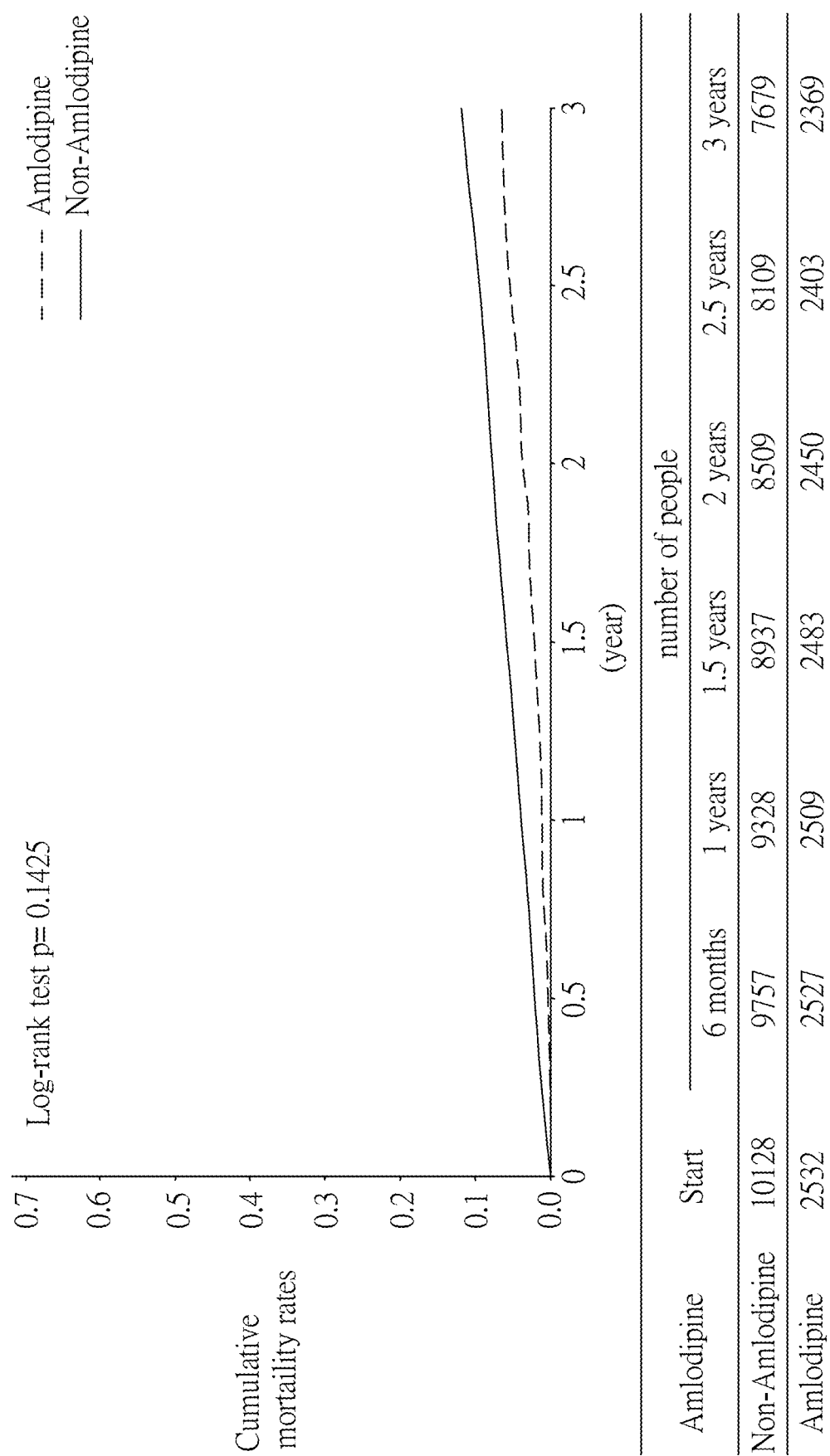
FIG. 6 shows the result of statistical analysis at various times after patients having breast cancer receive or receive no treatment with Amlodipine.
Figure 7:
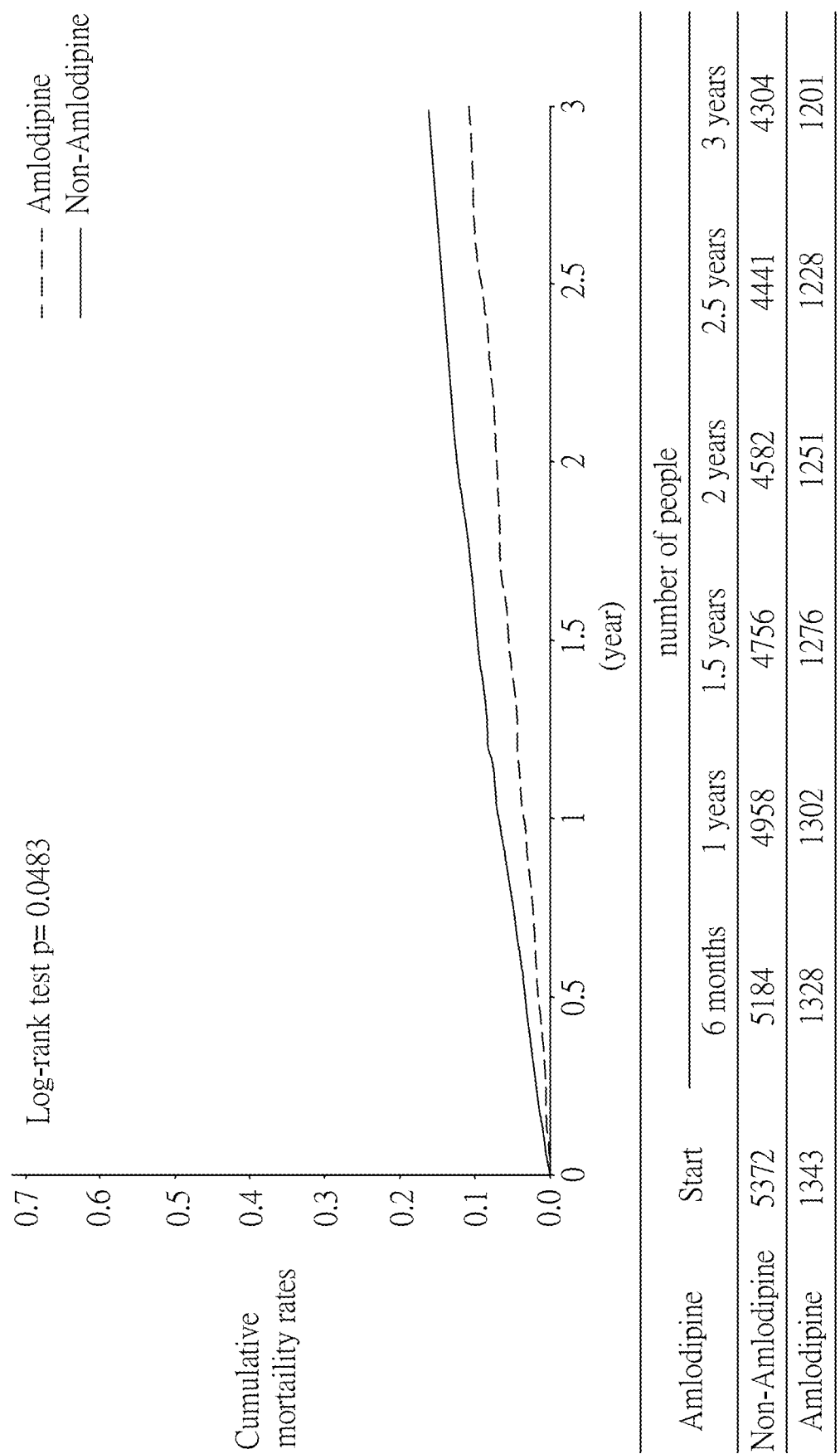
FIG. 7 shows the result of statistical analysis at various times after patients having cervical cancer receive or receive no treatment with Amlodipine.
Figure 8:
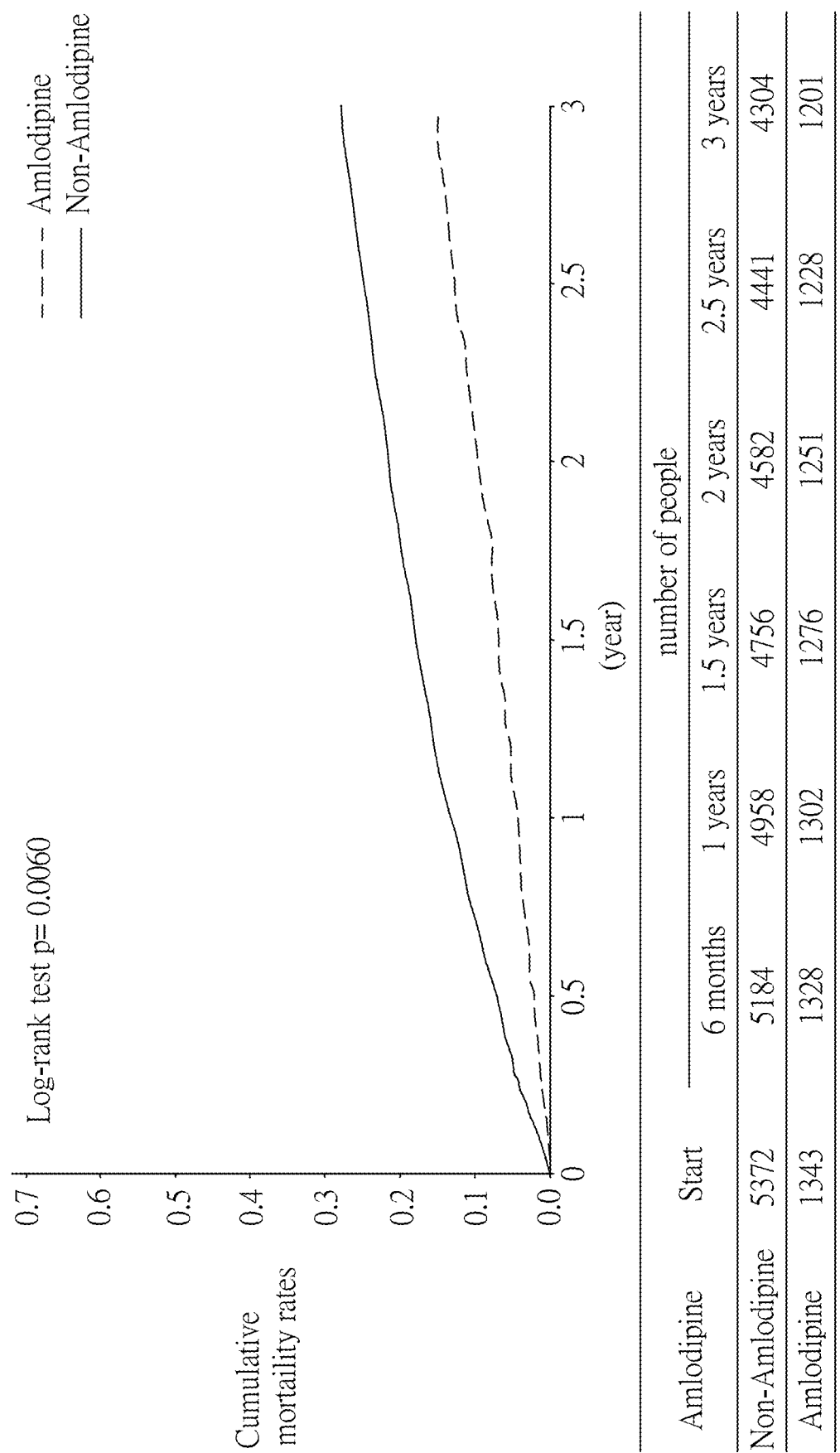
FIG. 8 shows the result of statistical analysis at various times after patients having bladder cancer receive or receive no treatment with Amlodipine.

The present invention will be further described below by way of examples in connection with the drawings.

Example 1: Statistical Analysis (I)

In this example, statistical analysis was performed on the statistics of the effects of Amlodipine in the treatment of cancers, using data from the National Health Insurance Research Database (NHIRD) covering detailed healthcare data for the population in Taiwan. Then, the diagnostic data at the time of admission in the database and the database of patients with registered major injuries were used, and statistical analysis was performed using data from patients with gastric cancer. The results are as shown in Table 1 below, in which 24/30 represents treatment with Amlodipine for at least 24 days within 30 days after cancer diagnosis, 48/60 represents treatment with Amlodipine for at least 48 days within 60 days after cancer diagnosis, and 72/90 represents treatment with Amlodipine for at least 72 days within 90 days after cancer diagnosis.

TABLE 1

| | Effect of Amlodipine in the treatment of cancers | | | | |
|---|---|---|---|---|---|
| | Day of treatment with | Number of patients | Cases of death | Crude HR | |
| Cancer type | Amlodipine | With/without Amlodipine | | HRs (95% C.I.) | P value |
| Gastric cancer | 24/30 | 1577/6308 | 727/3644 | 0.43 (0.39-0.47) | <.0001 |
| | 48/60 | 1324/5296 | 621/3097 | 0.43 (0.39-0.48) | <.0001 |
| | 72/90 | 1185/4740 | 549/2715 | 0.42 (0.38-0.47) | <.0001 |
| Colorectal cancer | 24/30 | 6673/26692 | 2713/11833 | 0.46 (0.44-0.49) | <.0001 |
| | 48/60 | 5705/22820 | 2283/10176 | 0.44 (0.42-0.47) | <.0001 |
| | 72/9 | 5044/20176 | 1999/8911 | 0.44 (0.42-0.47) | <.0001 |
| Liver cancer | 24/30 | 3084/12336 | 2292/8197 | 0.55 (0.53-0.59) | <.0001 |
| | 48/60 | 2598/10392 | 1928/6918 | 0.54 (0.51-0.57) | <.0001 |
| | 72/90 | 2297/9188 | 1704/5967 | 0.55 (0.52-0.58) | <.0001 |
| Pancreatic cancer | 24/30 | 235/940 | 192/729 | 0.62 (0.51-0.75) | <.0001 |
| | 48/60 | 196/784 | 161/618 | 0.63 (0.51-0.77) | <.0001 |
| | 72/90 | 171/684 | 144/503 | 0.71 (0.57-0.88) | 0.002 |
| Lung cancer | 24/30 | 2312/9248 | 1757/6375 | 0.66 (0.62-0.70) | <.0001 |
| | 48/60 | 1959/7836 | 1469/5358 | 0.62 (0.58-0.67) | <.0001 |
| | 72/9 | 1720/6880 | 1285/4725 | 0.62 (0.58-0.66) | <.0001 |
| Breast cancer | 24/30 | 4005/16020 | 1025/3825 | 0.54 (0.50-0.59) | <.0001 |
| | 48/60 | 3489/13956 | 885/3360 | 0.53 (0.48-0.57) | <.0001 |
| | 72/90 | 3145/12580 | 786/3085 | 0.50 (0.46-0.55) | <.0001 |
| Cervical cancer | 24/30 | 2769/11076 | 815/3868 | 0.50 (0.46-0.55) | <.0001 |
| | 48/60 | 2320/9280 | 670/3180 | 0.51 (0.46-0.56) | <.0001 |
| | 72/90 | 2041/8164 | 589/2889 | 0.46 (0.42-0.51) | <.0001 |
| Bladder cancer | 24/30 | 1930/7720 | 889/3237 | 0.54 (0.50-0.59) | <.0001 |
| | 48/60 | 1634/6536 | 754/2725 | 0.55 (0.50-0.60) | <.0001 |
| | 72/90 | 1421/5684 | 648/2360 | 0.55 (0.50-0.61) | <.0001 |

It can be seen from Table 1 that administration of Amlodipine to cancer patients can effectively reduce the mortality of cancer patients, and, in particular, it can be known from Table 1 that the longer the duration of the administration time is, the lower the mortality rate is.

Example 2: Statistical Analysis (II)

The dose of Amlodipine used in Example 1 was at least 120 mg/30 days. Therefore, in order to obtain the minimum effective dose, the survival rate of patients treated with Amlodipine for days in 90 days after cancer diagnosis was further statistically analyzed. The results are shown in Table 2 below.

TABLE 2

| Analysis of survival rate after treatment with Amlodipine for 20 days within 90 days after diagnosis | | | | |
|---|---|---|---|---|
| Cancer type | With Amlodipine/ death | Without Amlodipine/ death | Crude HR | |
| | | | HRs (95% C.I.) | p-value |
| Gastric cancer | 1147/625 | 4588/2571 | 0.73 (0.66-0.80) | <.0001 |
| Colorectal cancer | 4645/2158 | 18580/8241 | 0.76 (0.72-0.80) | <.0001 |
| Liver cancer | 2865/2189 | 11460/7490 | 0.73 (0.69-0.77) | <.0001 |
| Pancreatic cancer | 227/192 | 908/658 | 0.77 (0.65-0.93) | 0.0059 |
| Lung cancer | 2221/1771 | 8884/6013 | 0.85 (0.80-0.90) | <.0001 |
| Breast cancer | 2532/733 | 10128/2601 | 0.91 (0.83-0.99) | 0.0339 |
| Cervical cancer | 1343/465 | 5372/1693 | 1.00 (0.89-1.11) | 0.9418 |
| Bladder cancer | 1396/678 | 5584/2375 | 0.82 (0.75-0.90) | <.0001 |

The survival rate was analyzed for each cancer. The results are shown in FIGS. 1-8, respectively.

The results of this example show that administration of Amlodipine does increase the survival rate of cancer patients compared with cancer patients receiving no treatment with Amlodipine, and can effectively reduce the mortality of cancer patients as shown by the long-term follow-up results (3 years). In addition, from the results of this example, it can be seen that the use of 100 mg of Amlodipine in 90 days can achieve the effect of increasing the survival rate of cancer patients.

Example 3: Cell Assay

Two liver cancer cell lines HepG2 and Hep3B were cultured. The medium used for the culture of the cells was DMEM medium containing 10% fetal bovine serum, 10,000 U/ml penicillin and 10,000 μg/ml streptomycin. The culture occurred in an environment at 37° C. with 5% $CO_2$, and the medium was changed every 2-3 days during the culture.

After the cells were cultured to about 70% confluence, they were treated with various concentrations of Amlodipine: 0, 1.5625, 3.125, 6.25, 12.5, 25, and 50 μM for various times: 48, and 72 hrs. After the experiment, the viability of each liver cancer cell line was observed and the cell viability and cell cycle were analyzed.

Example 4: Cell Viability of Liver Cancer Cell Lines

Figure 9:
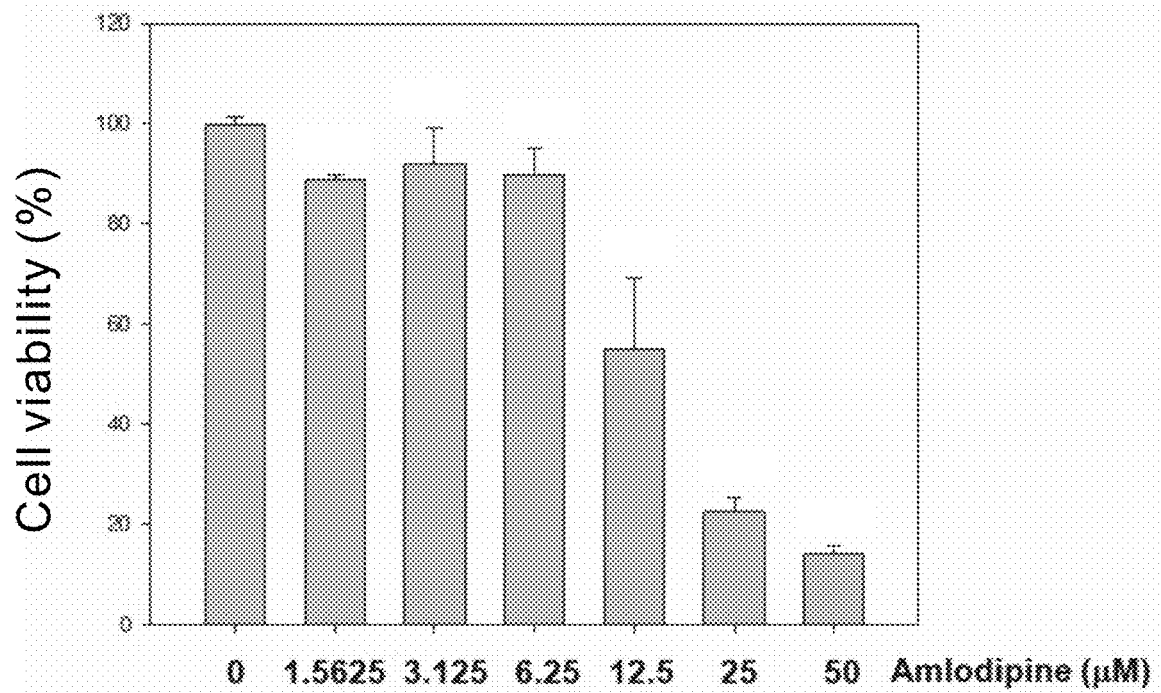
FIG. 9 shows the result of cell viability of HepG2 cells detected after treatment with various concentrations of Amlodipine for 72 hrs.
Figure 10:
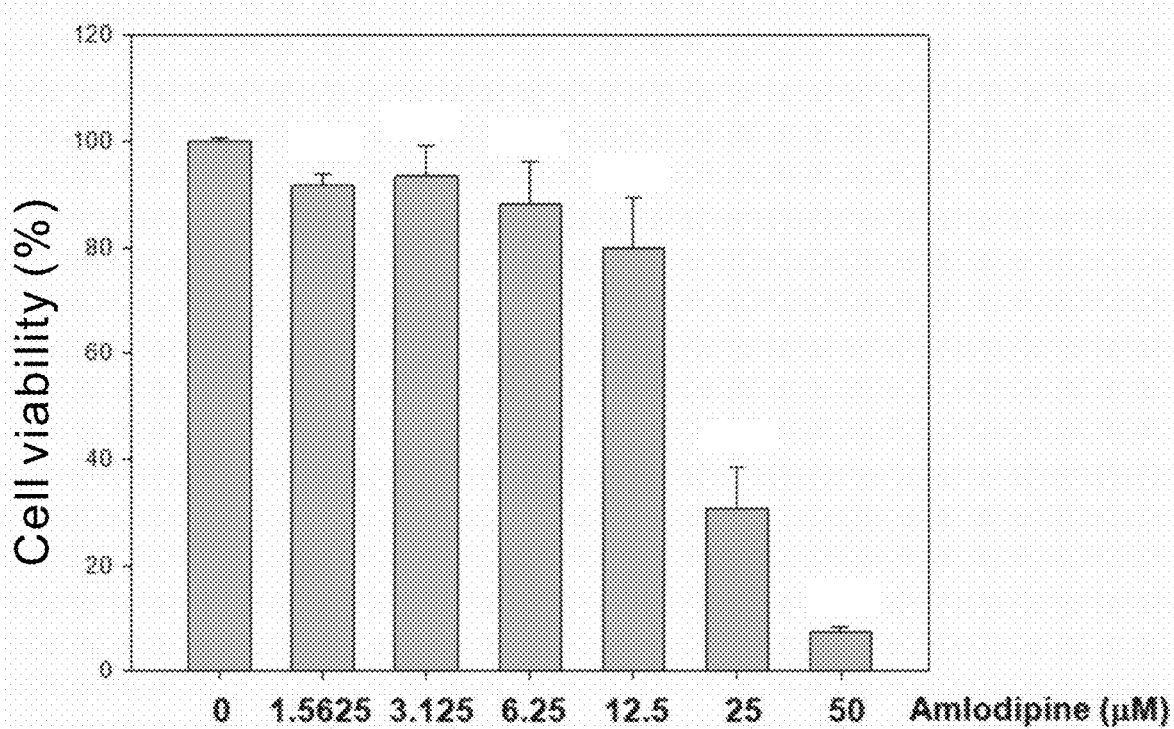
FIG. 10 shows the result of cell viability of Hep3B cells detected after treatment with various concentrations of Amlodipine for 72 hrs.
Figure 11A:
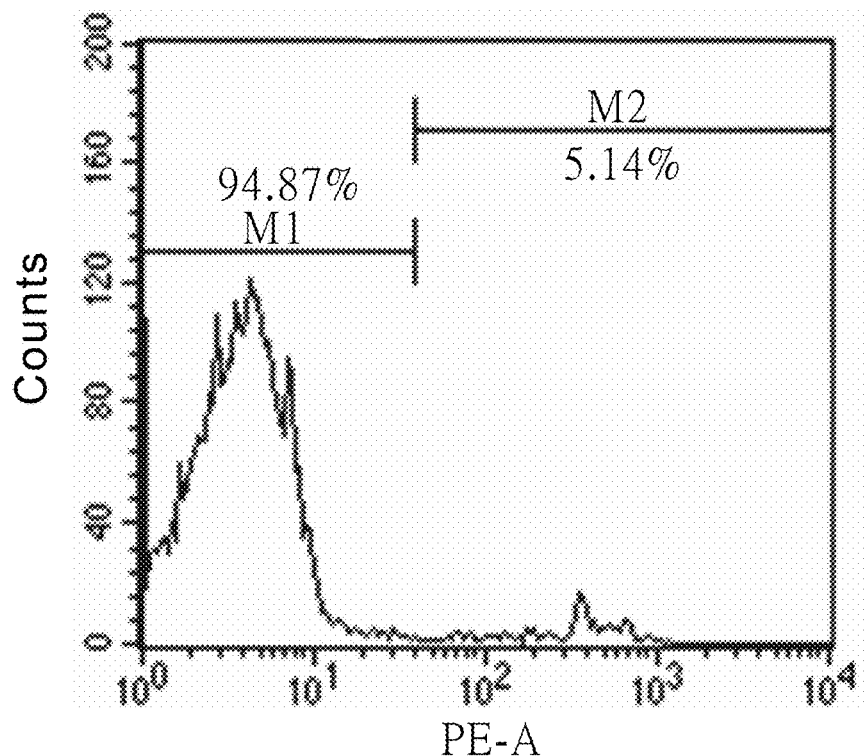
FIG. 11A shows the result of cell viability by flow cytometry of HepG2 cells receiving no treatment with Amlodipine.
Figure 11B:
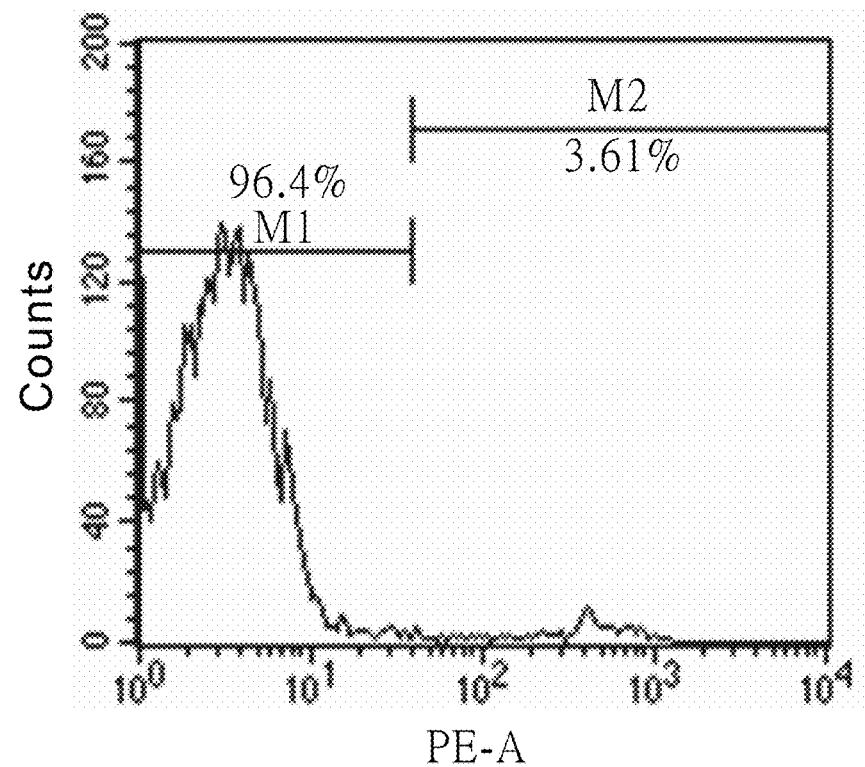
FIG. 11B shows the result of cell viability by flow cytometry of HepG2 cells after treatment with 1.5625 μM Amlodipine for 48 hrs.
Figure 11C:
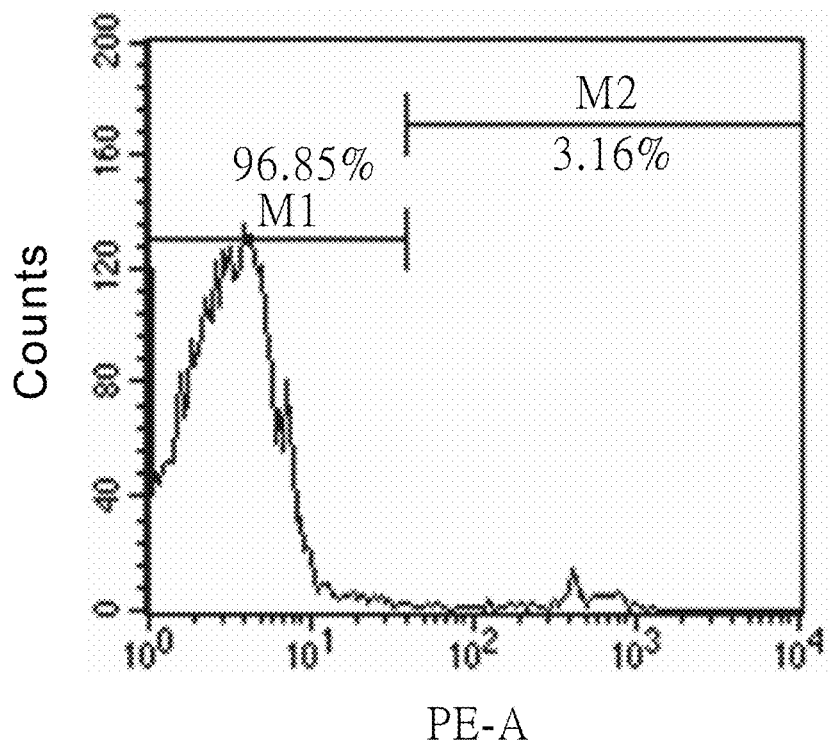
FIG. 11C shows the result of cell viability by flow cytometry of HepG2 cells after treatment with 3.125 μM Amlodipine for 48 hrs.
Figure 11D:
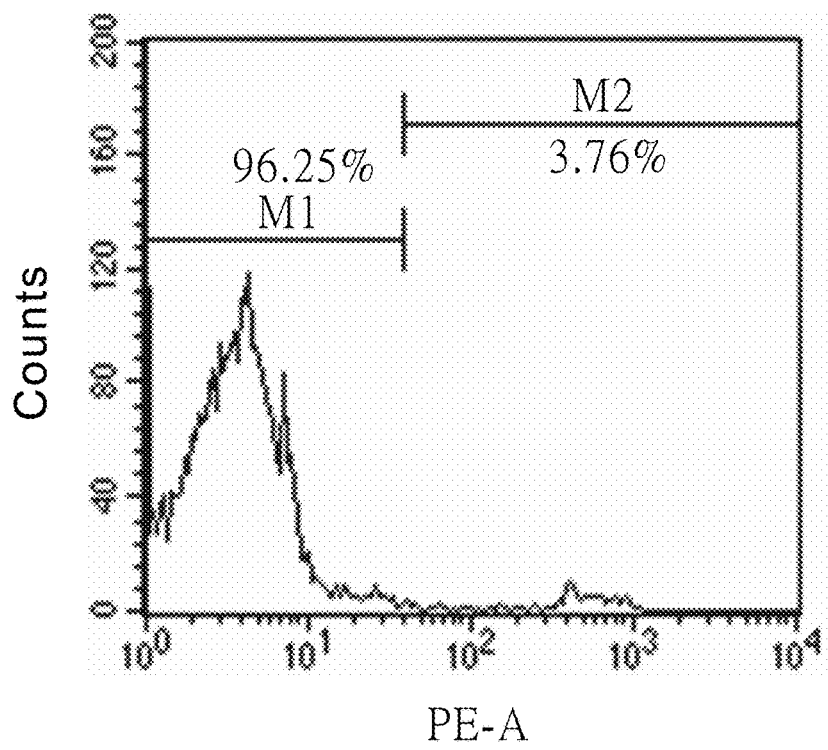
FIG. 11D shows the result of cell viability by flow cytometry of HepG2 cells after treatment with 6.25 μM Amlodipine for 48 hrs.
Figure 11E:
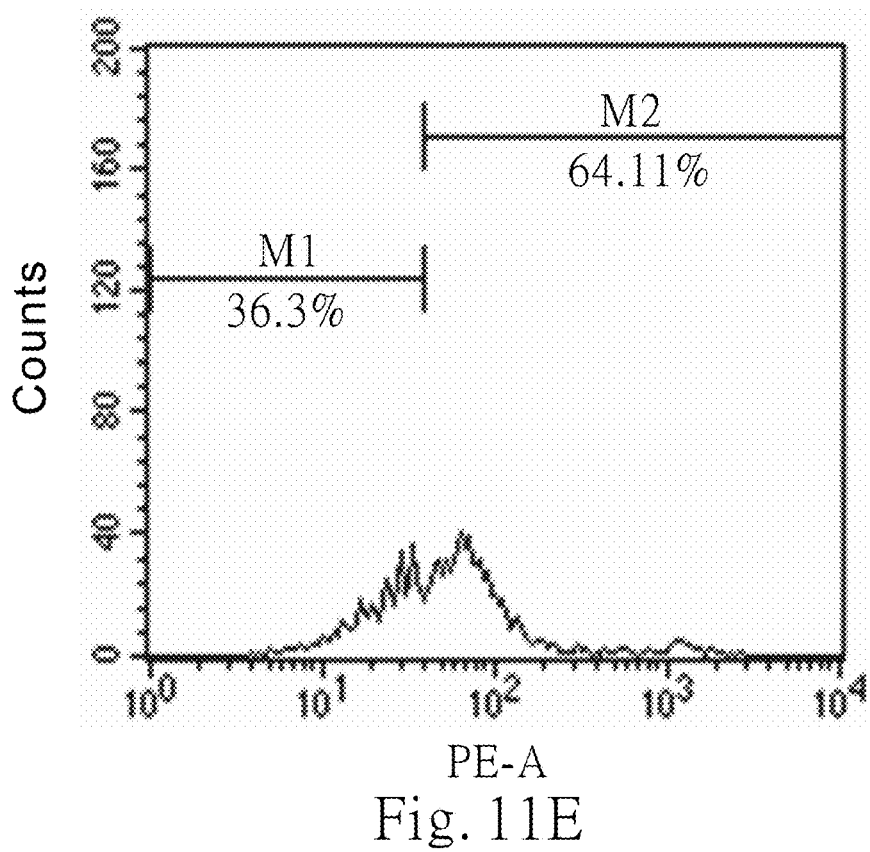
FIG. 11E shows the result of cell viability by flow cytometry of HepG2 cells after treatment with 12.5 µM Amlodipine for 48 hrs.
Figure 11F:
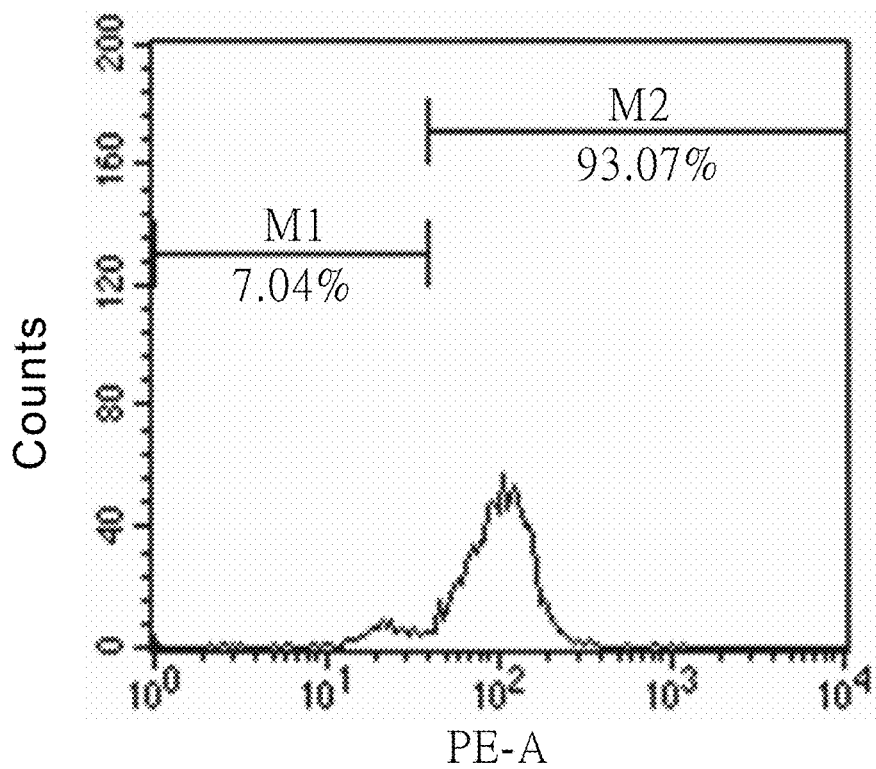
FIG. 11F shows the result of cell viability by flow cytometry of HepG2 cells after treatment with 25 µM Amlodipine for 48 hrs.
Figure 12:
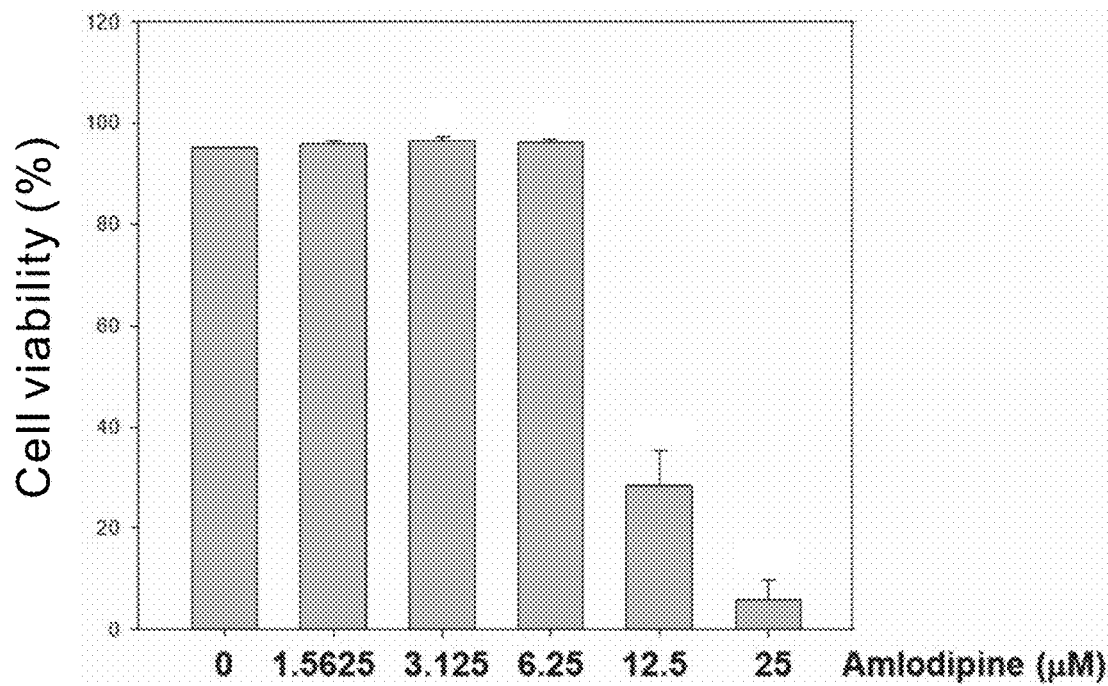
FIG. 12 shows the result of cell viability of HepG2 cells detected after treatment with various concentrations of Amlodipine for 48 hrs.
Figure 13A:
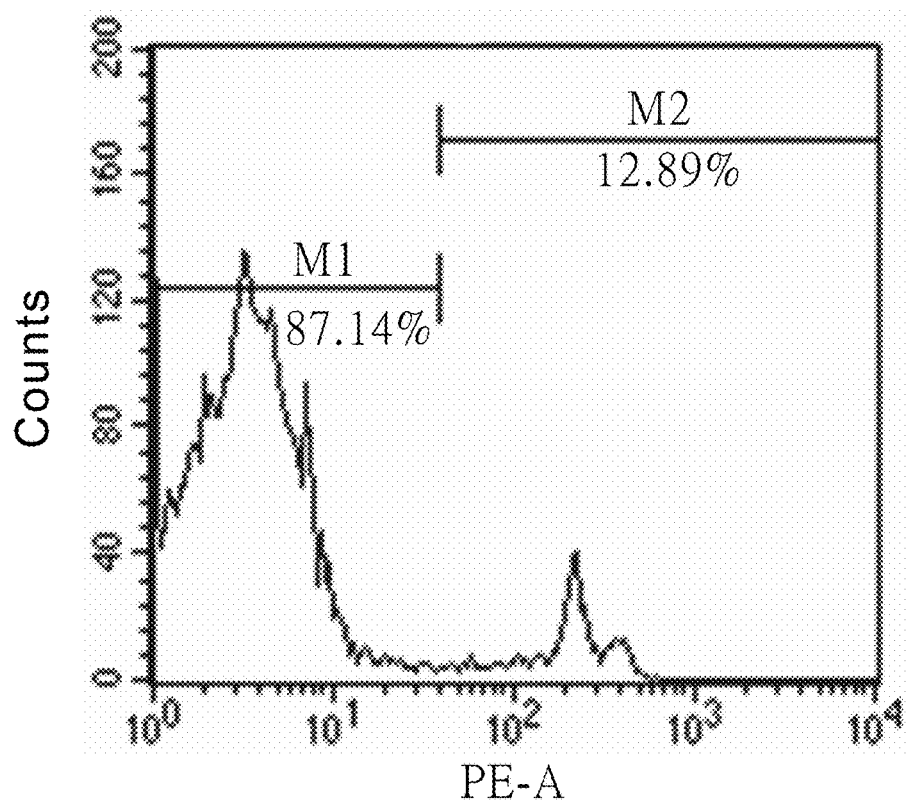
FIG. 13A shows the result of cell viability by flow cytometry of Hep3B cells receiving no treatment with Amlodipine (Batch 1).
Figure 13B:
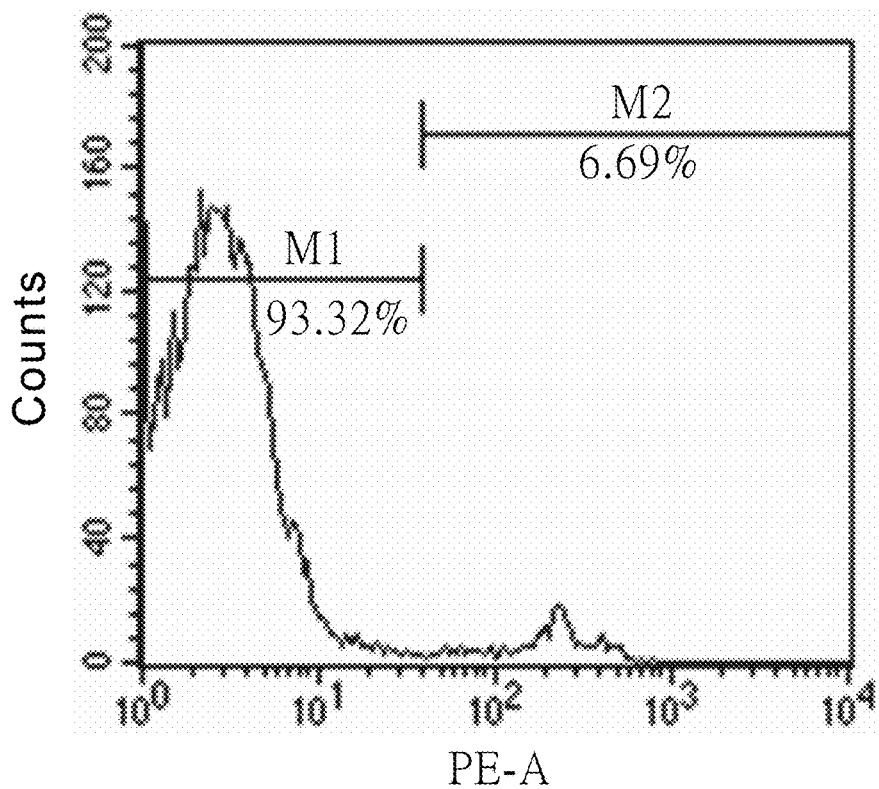
FIG. 13B shows the result of cell viability by flow cytometry of Hep3B cells (Batch 1) after treatment with 1.5625 µM Amlodipine for 48 hrs.
Figure 13C:
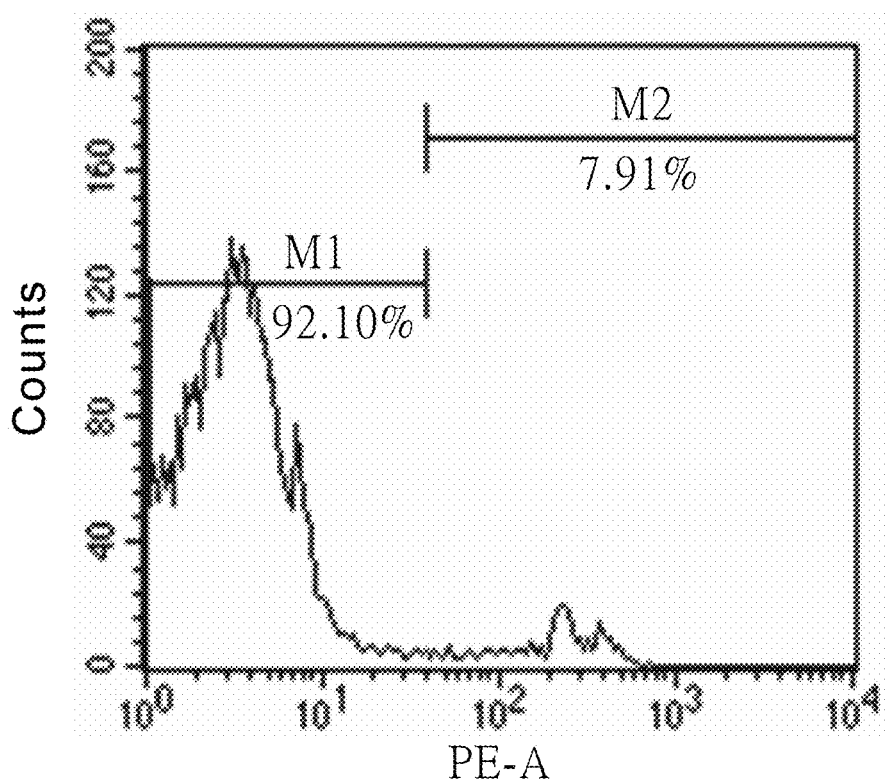
FIG. 13C shows the result of cell viability by flow cytometry of Hep3B cells (Batch 1) after treatment with 3.125 µM Amlodipine for 48 hrs.
Figure 13D:
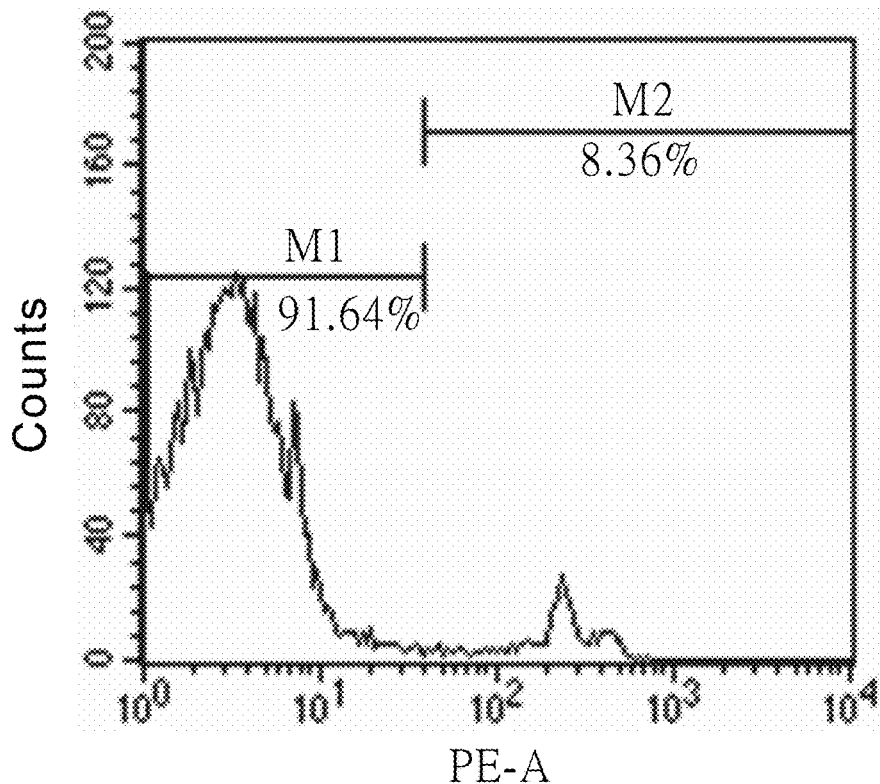
FIG. 13D shows the result of cell viability by flow cytometry of Hep3B cells (Batch 1) after treatment with 6.25 µM Amlodipine for 48 hrs.
Figure 13E:
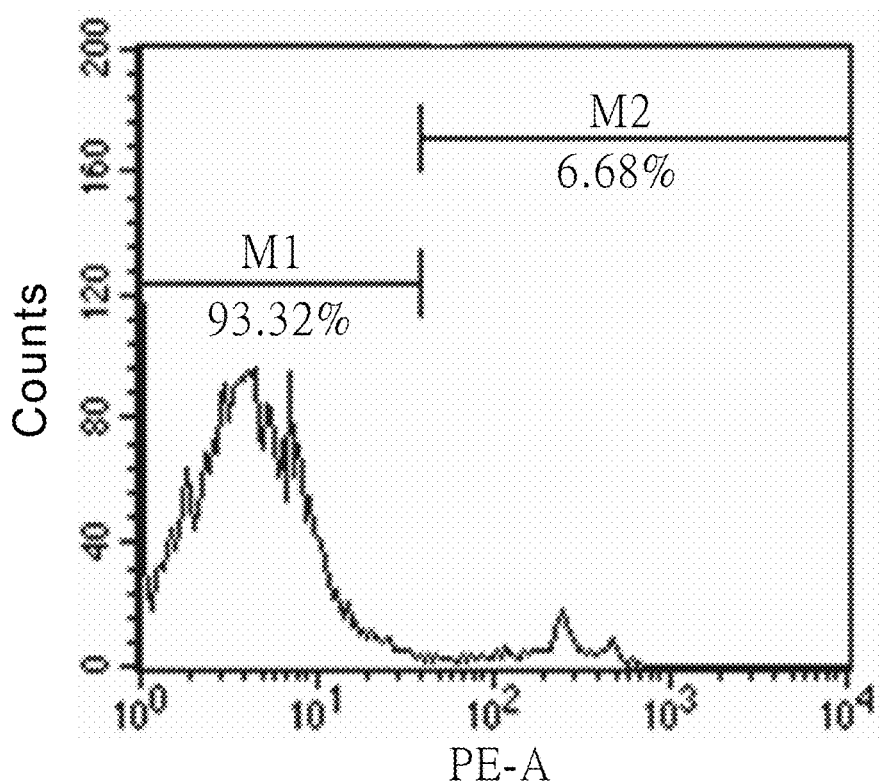
FIG. 13E shows the result of cell viability by flow cytometry of Hep3B cells (Batch 1) after treatment with 12.5 µM Amlodipine for 48 hrs.
Figure 13F:
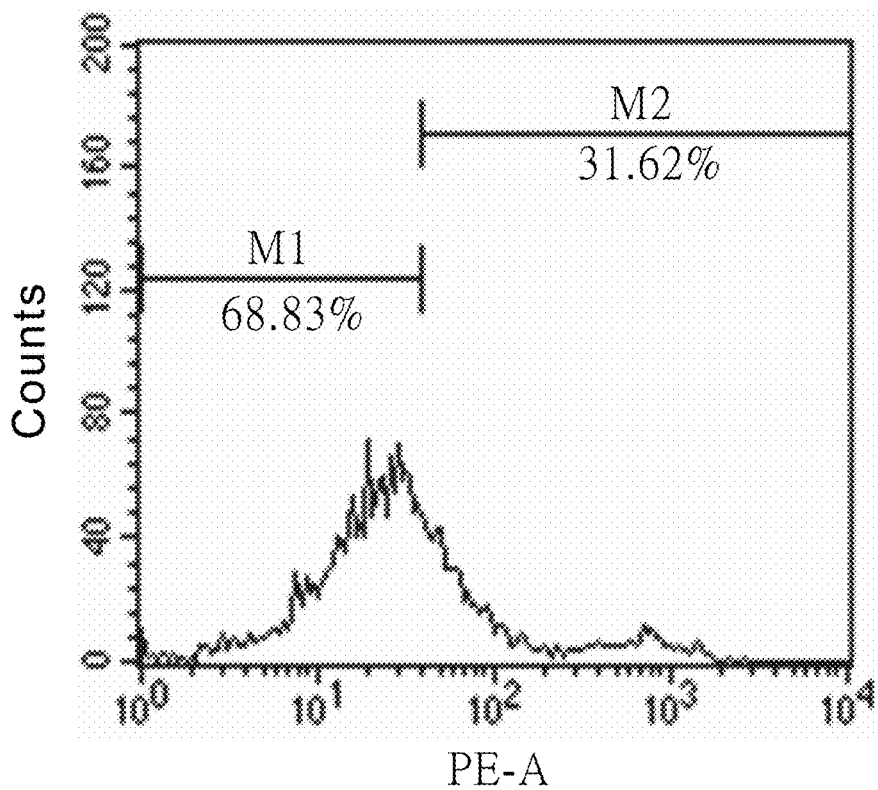
FIG. 13F shows the result of cell viability by flow cytometry of Hep3B cells (Batch 1) after treatment with 25 µM Amlodipine for 48 hrs.
Figure 14A:
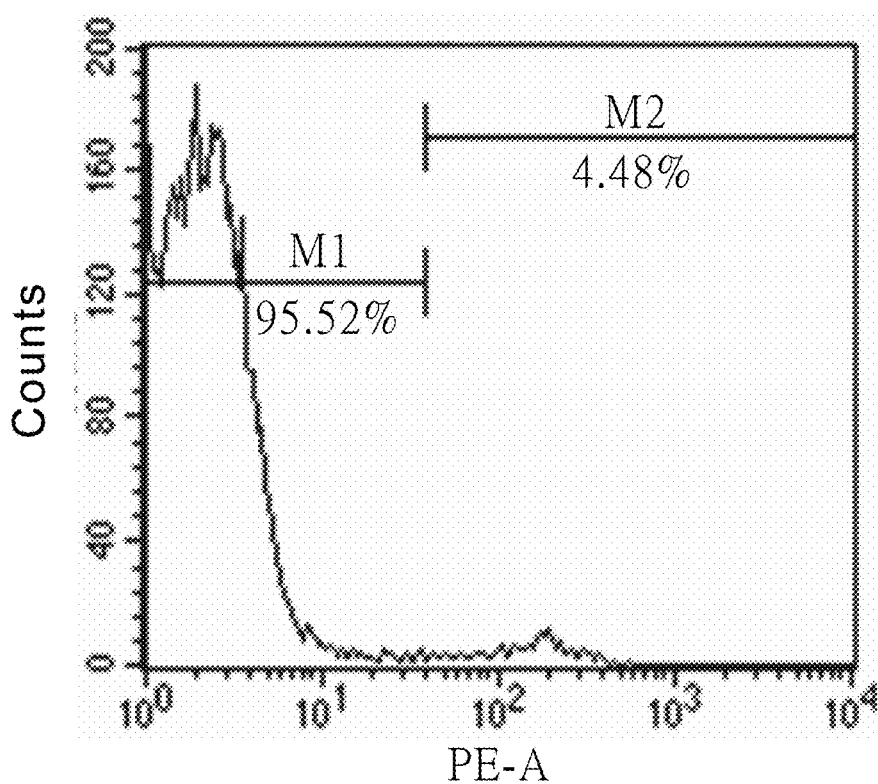
FIG. 14A shows the result of cell viability by flow cytometry of Hep3B cells receiving no treatment with Amlodipine (Batch 2).
Figure 14B:
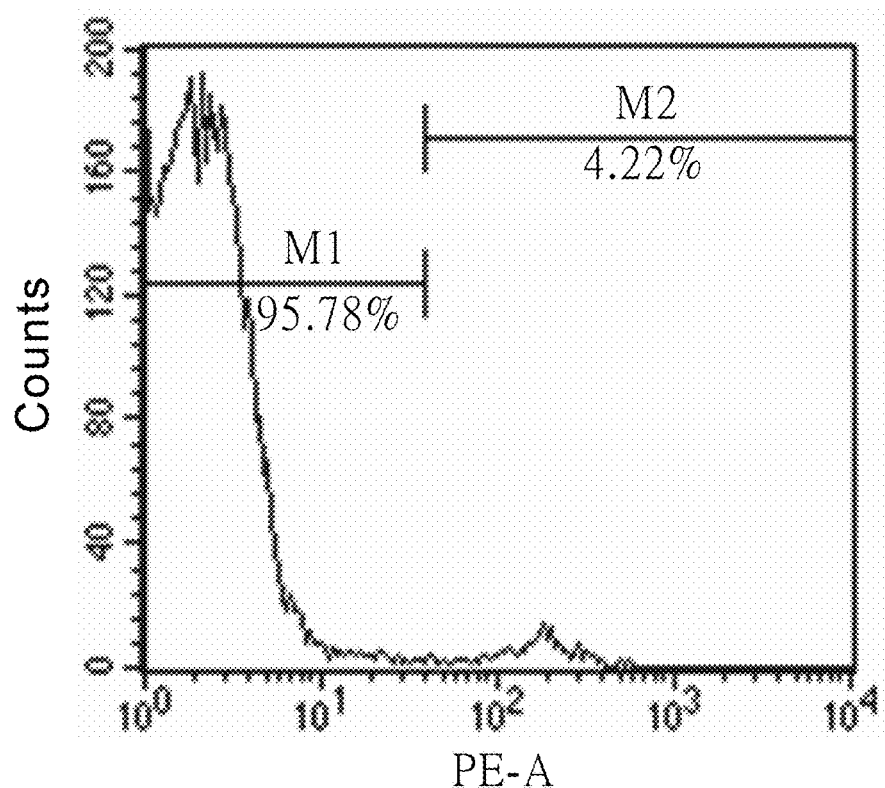
FIG. 14B shows the result of cell viability by flow cytometry of Hep3B cells (Batch 2) after treatment with 1.5625 µM Amlodipine for 48 hrs.
Figure 14C:
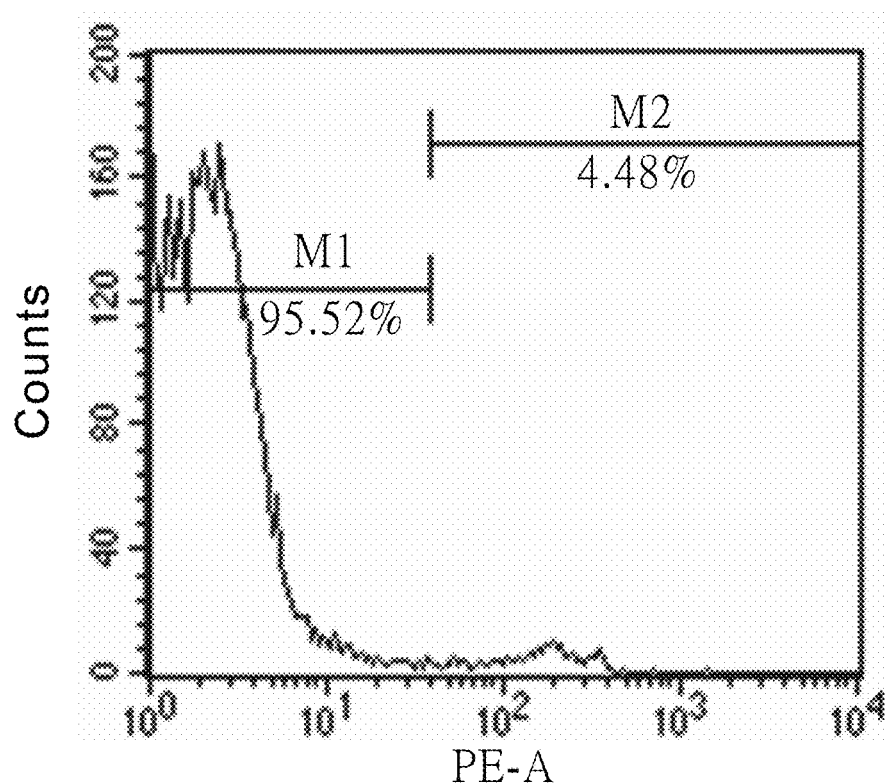
FIG. 14C shows the result of cell viability by flow cytometry of Hep3B cells (Batch 2) after treatment with 3.125 µM Amlodipine for 48 hrs.
Figure 14D:
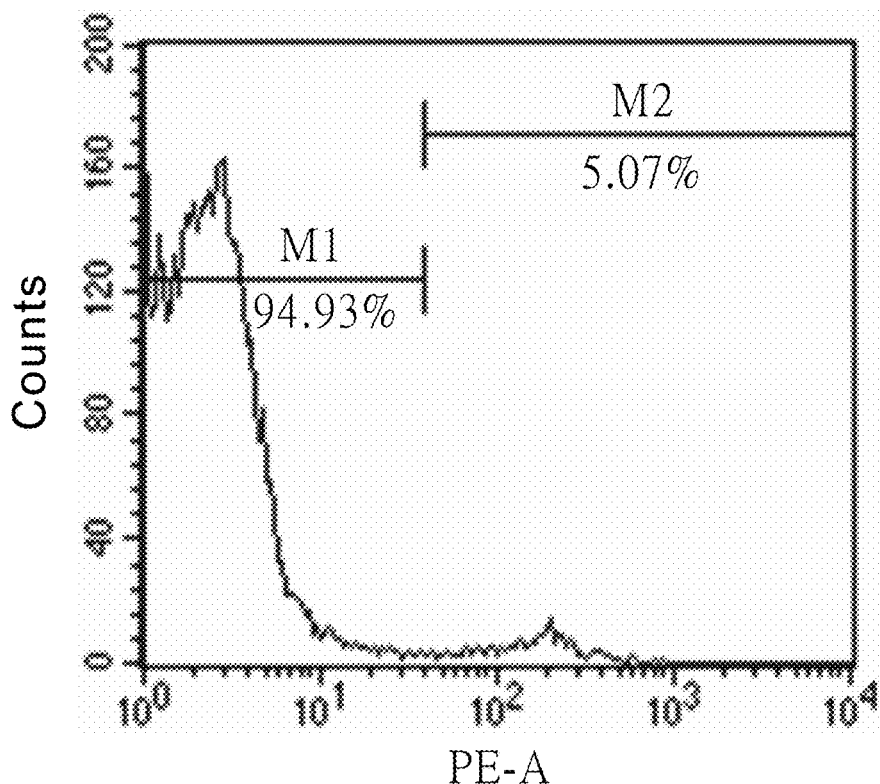
FIG. 14D shows the result of cell viability by flow cytometry of Hep3B cells (Batch 2) after treatment with 6.25 µM Amlodipine for 48 hrs.
Figure 14E:
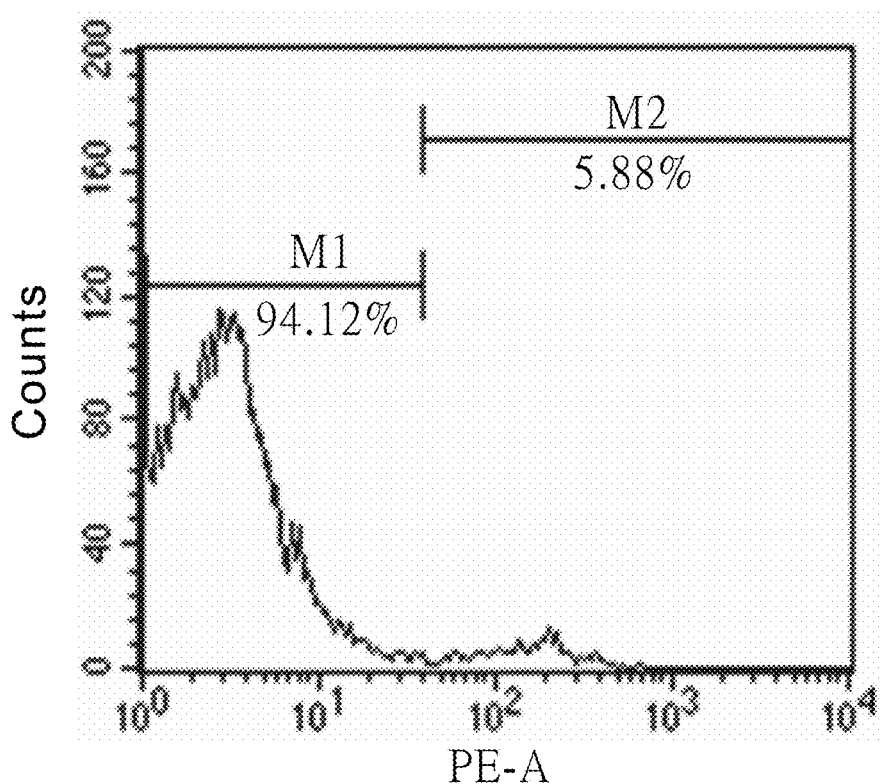
FIG. 14E shows the result of cell viability by flow cytometry of Hep3B cells (Batch 2) after treatment with 12.5 µM Amlodipine for 48 hrs.
Figure 14F:
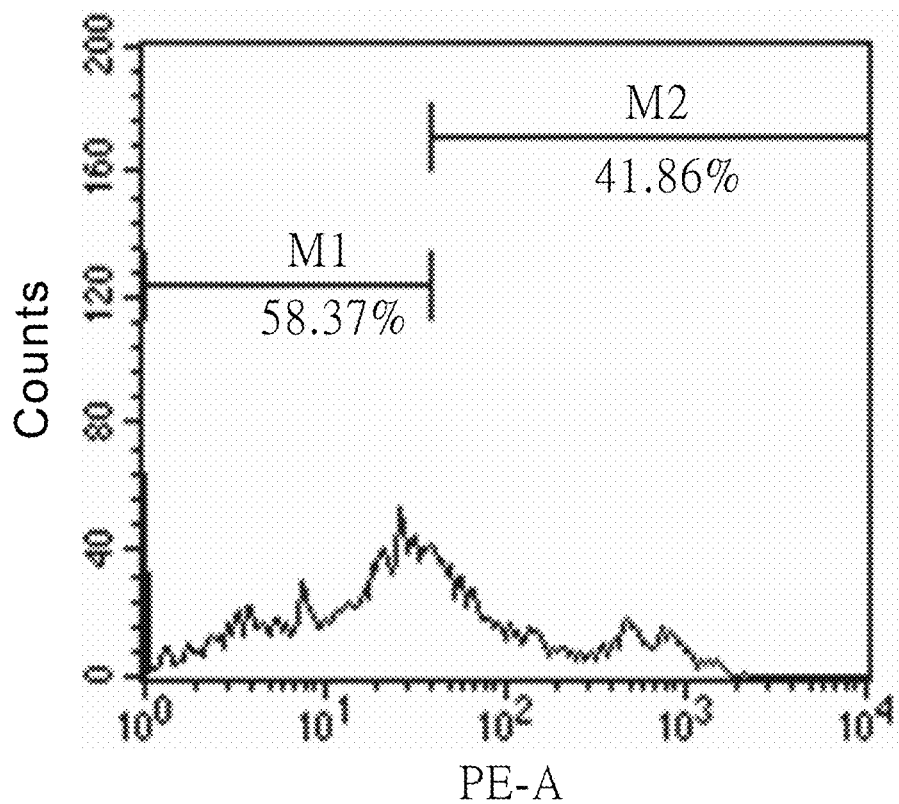
FIG. 14F shows the result of cell viability by flow cytometry of Hep3B cells (Batch 2) after treatment with 25 µM Amlodipine for 48 hrs.
Figure 15:
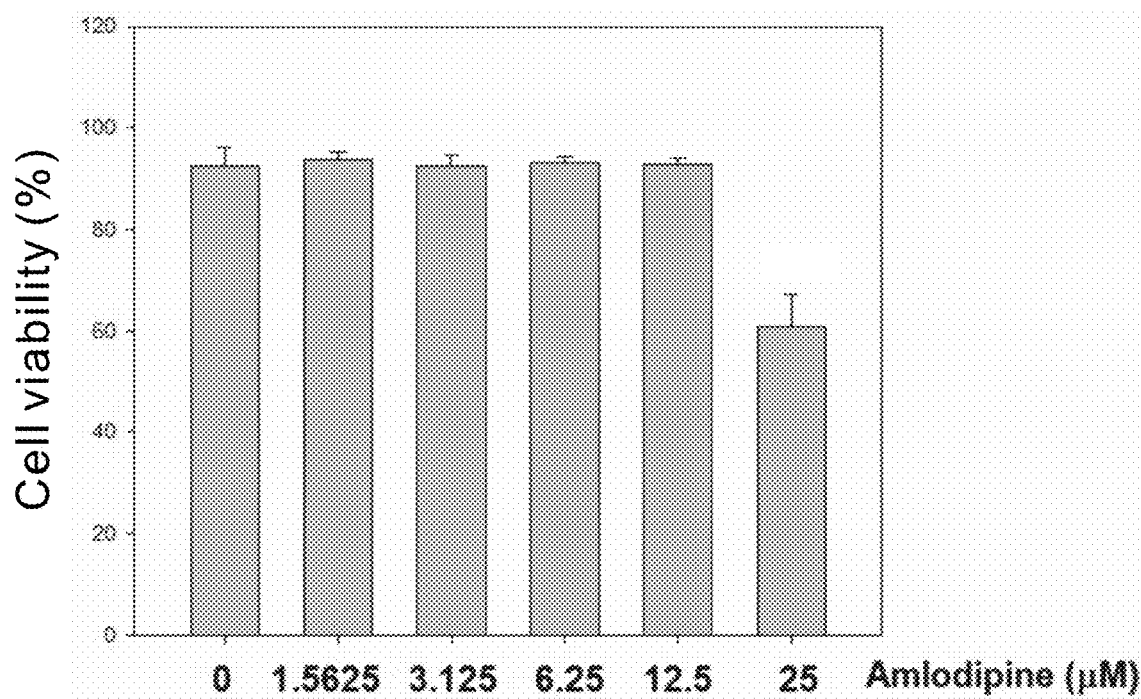
FIG. 15 shows the result of cell viability of Hep3B cells detected after treatment with various concentrations of Amlodipine for 48 hrs.
Figure 16A:
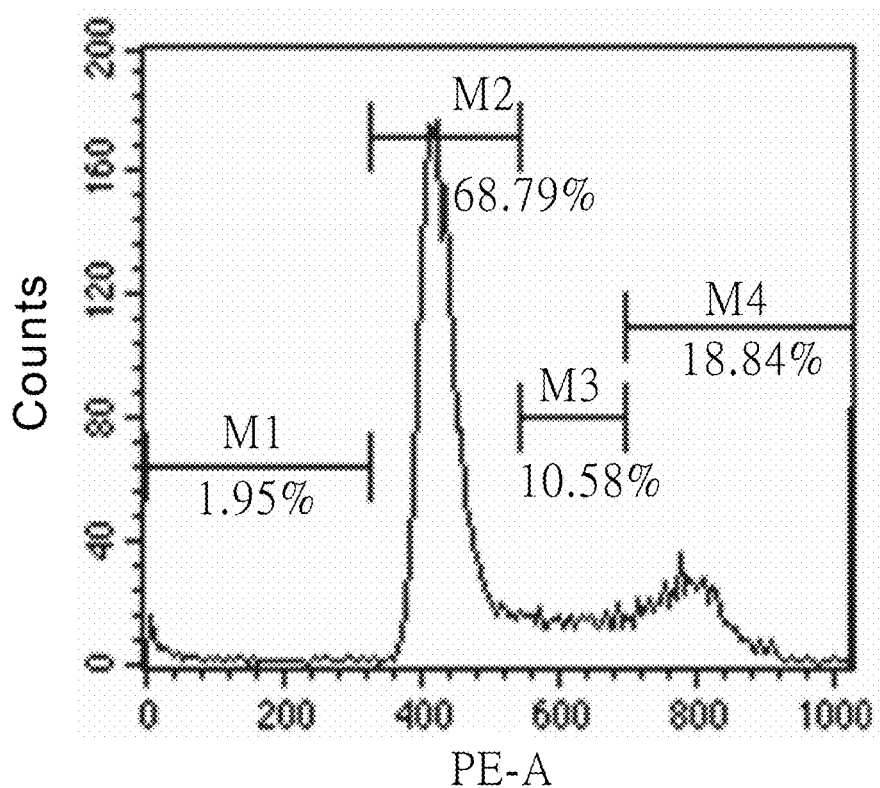
FIG. 16A shows the detection result of cell cycle of HepG2 cells receiving no treatment with Amlodipine.
Figure 16B:
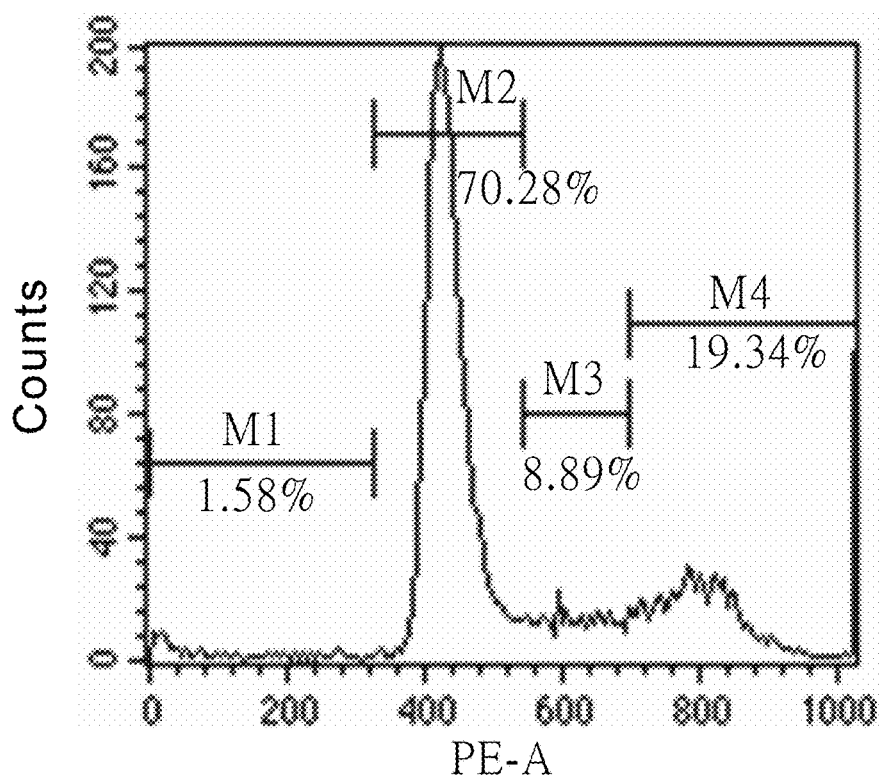
FIG. 16B shows the detection result of cell cycle of HepG2 cells after treatment with 1.5625 µM Amlodipine.
Figure 16C:
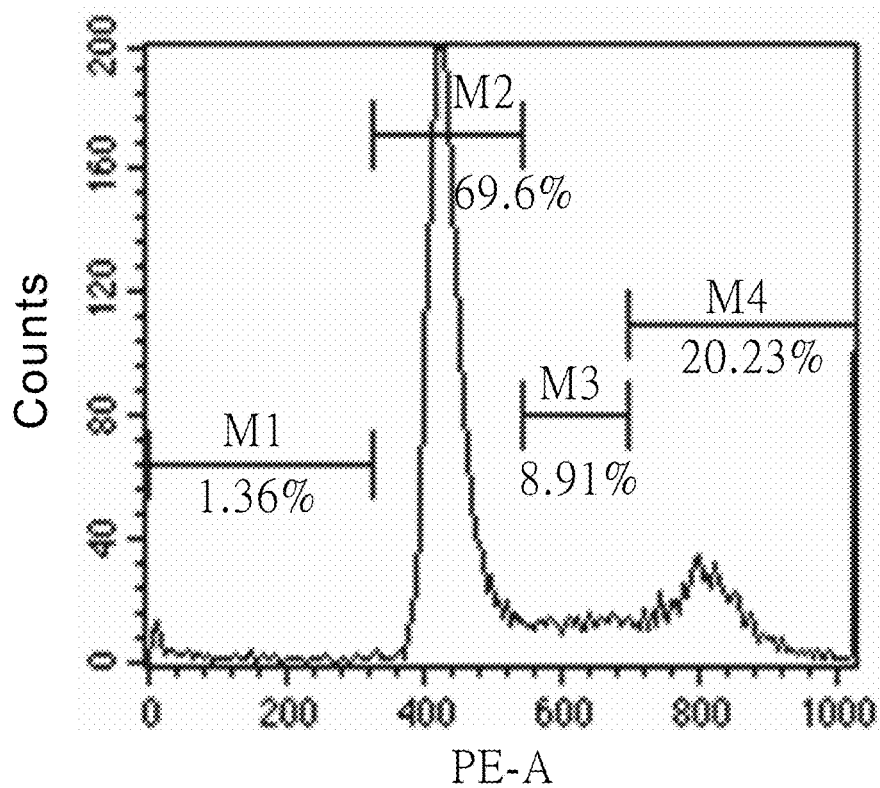
FIG. 16C shows the detection result of cell cycle of HepG2 cells after treatment with 3.125 µM Amlodipine.
Figure 16D:
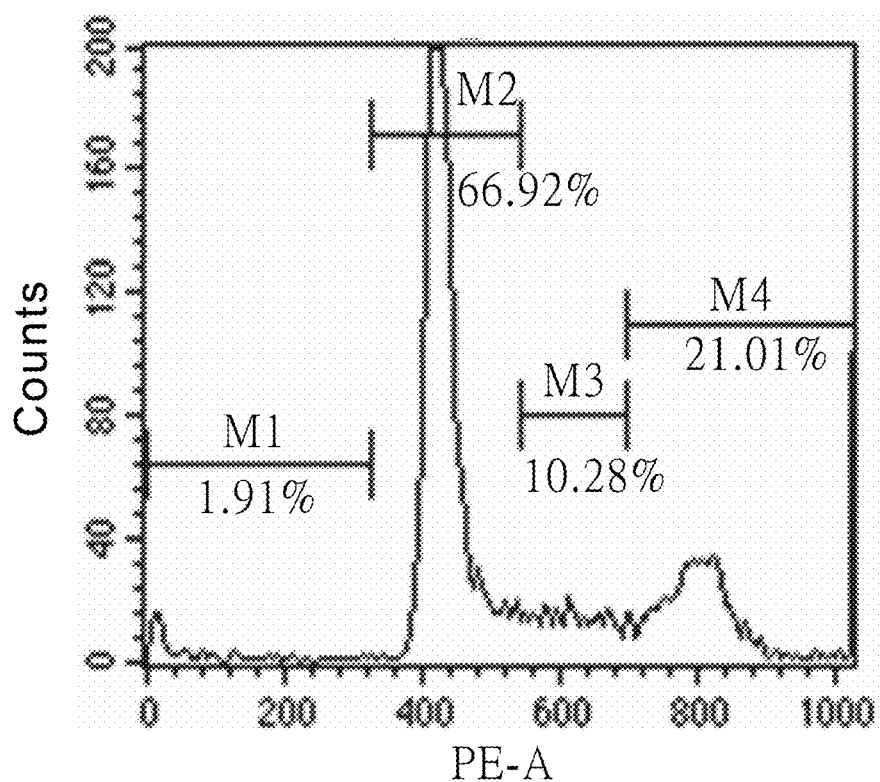
FIG. 16D shows the detection result of cell cycle of HepG2 cells after treatment with 6.25 µM Amlodipine.
Figure 16E:
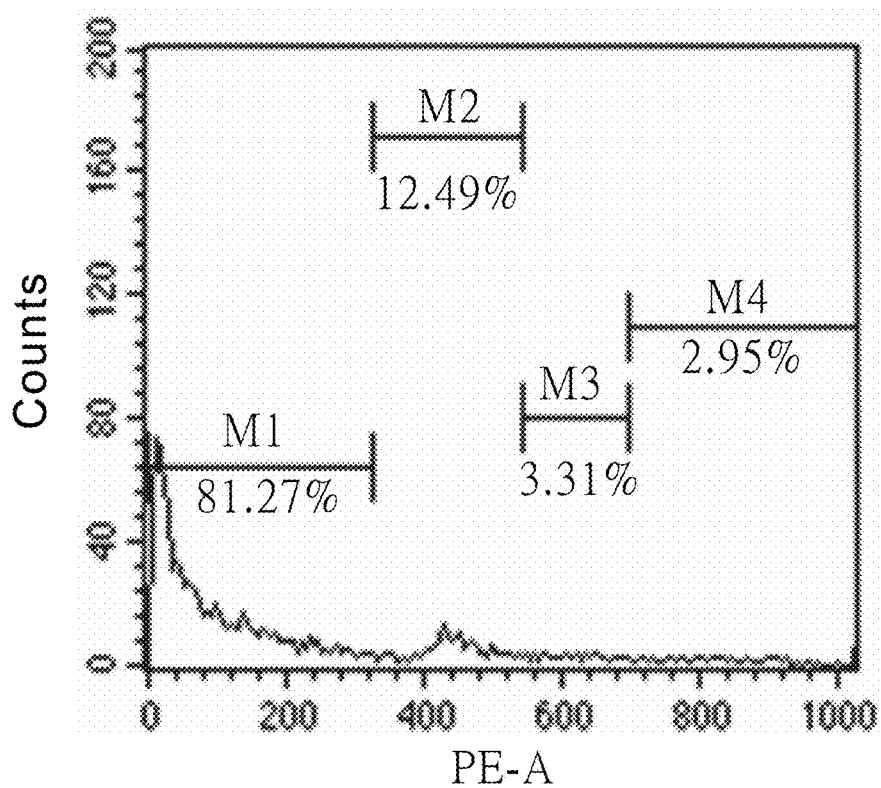
FIG. 16E shows the detection result of cell cycle of HepG2 cells after treatment with 12.5 µM Amlodipine.
Figure 16F:
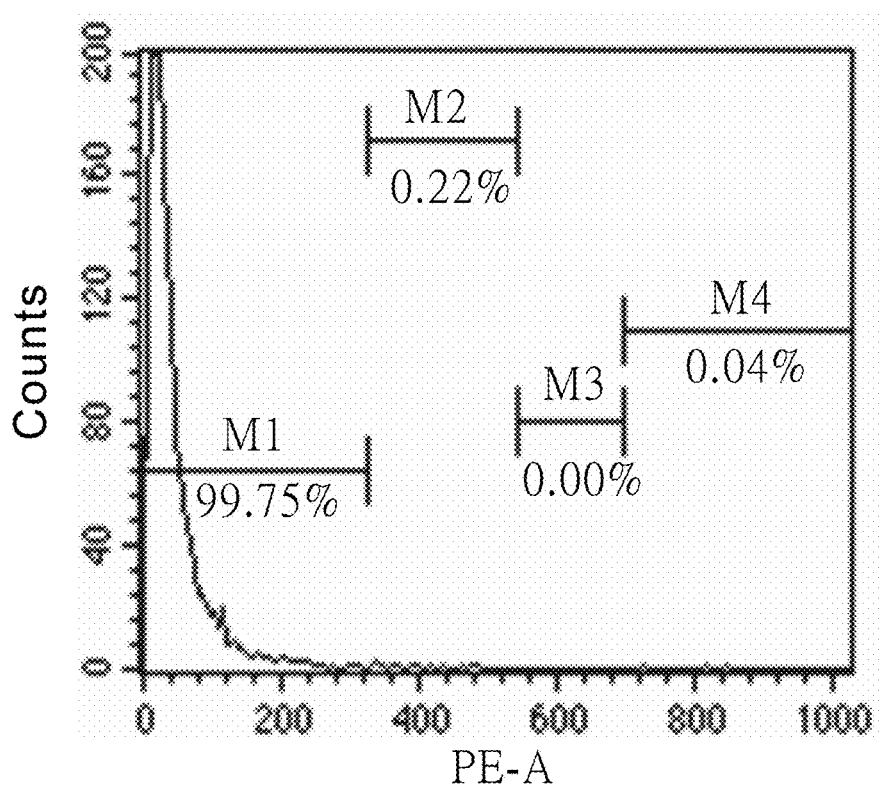
FIG. 16F shows the detection result of cell cycle of HepG2 cells after treatment with 25 µM Amlodipine.
Figure 17:
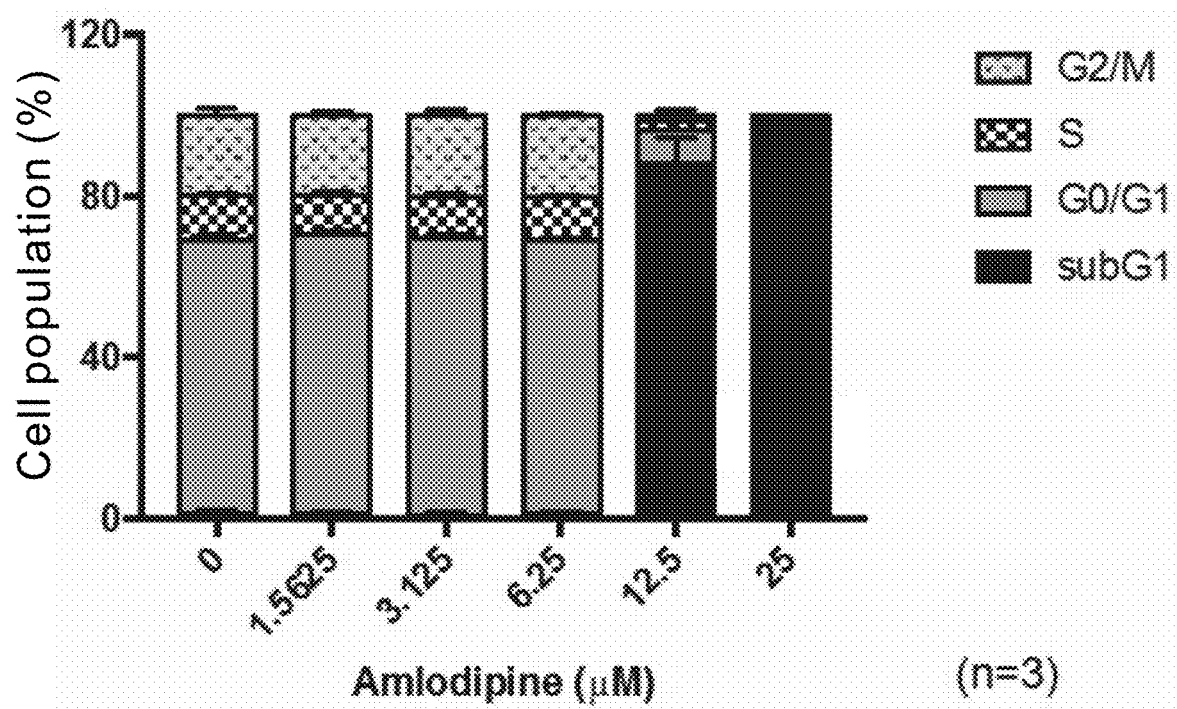
FIG. 17 shows the result of cell cycle by flow cytometry of HepG2 cells after treatment with various concentrations of Amlodipine.
Figure 18A:
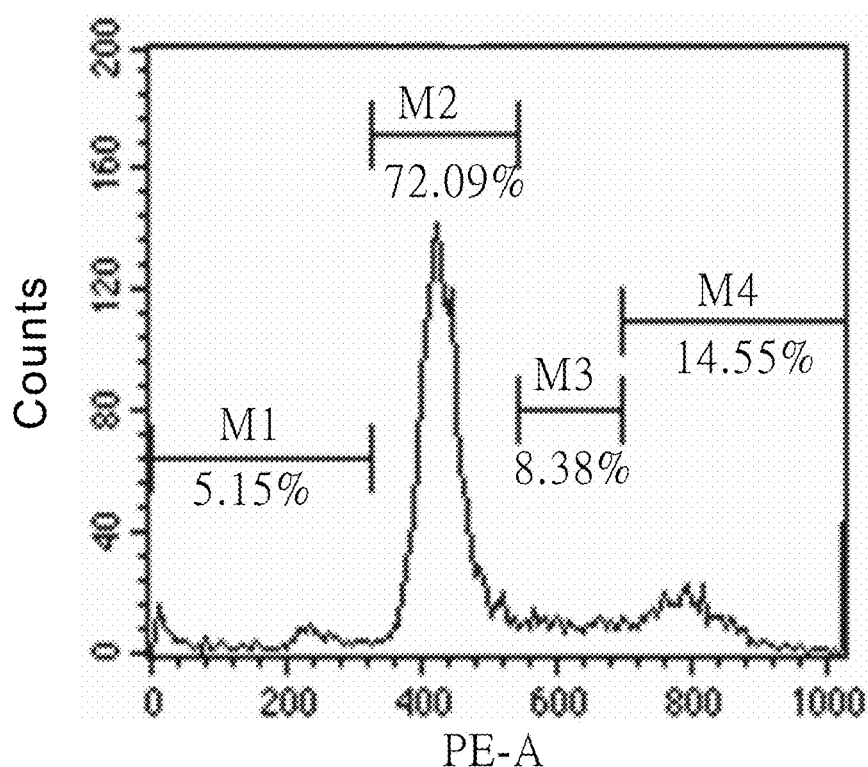
FIG. 18A shows the detection result of cell cycle of Hep3B cells receiving no treatment with Amlodipine.
Figure 18B:
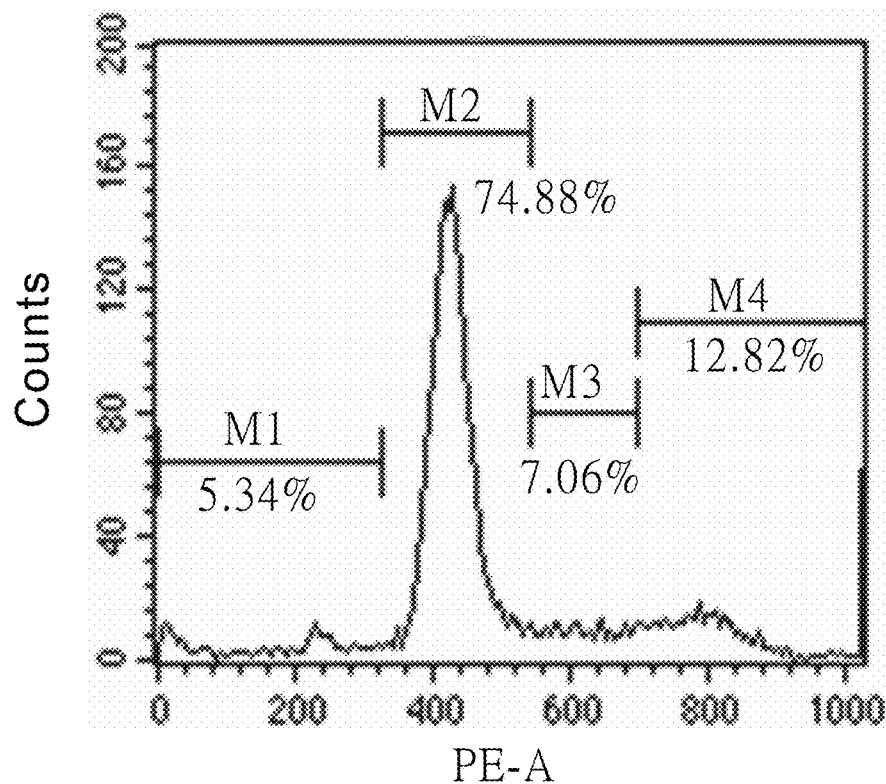
FIG. 18B shows the detection result of cell cycle of Hep3B cells after treatment with 1.5625 µM Amlodipine.
Figure 18C:
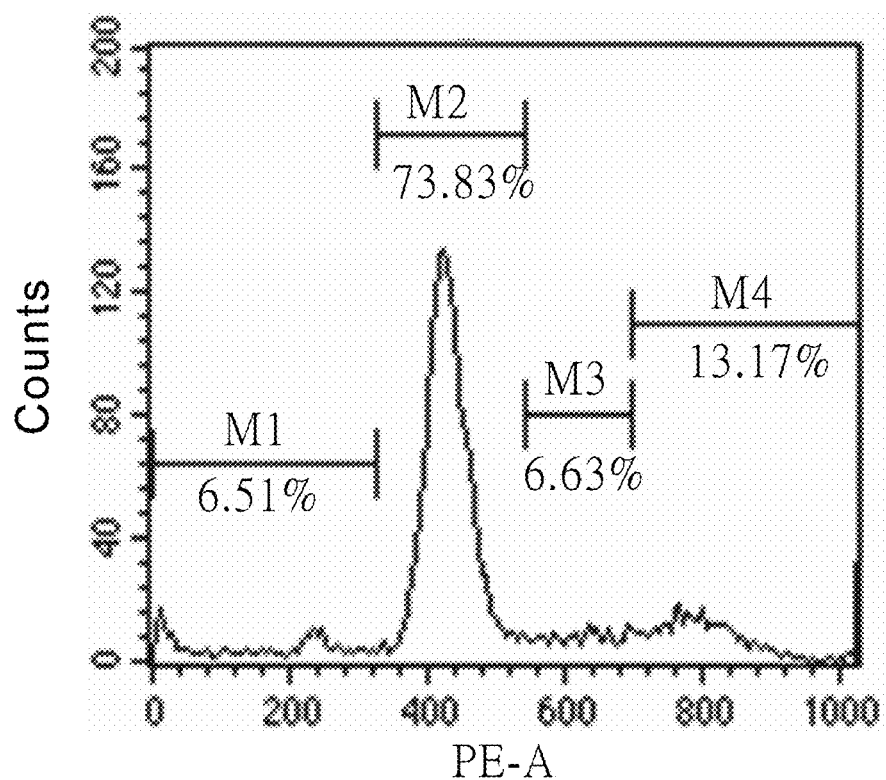
FIG. 18C shows the detection result of cell cycle of Hep3B cells after treatment with 3.125 µM Amlodipine.
Figure 18D:
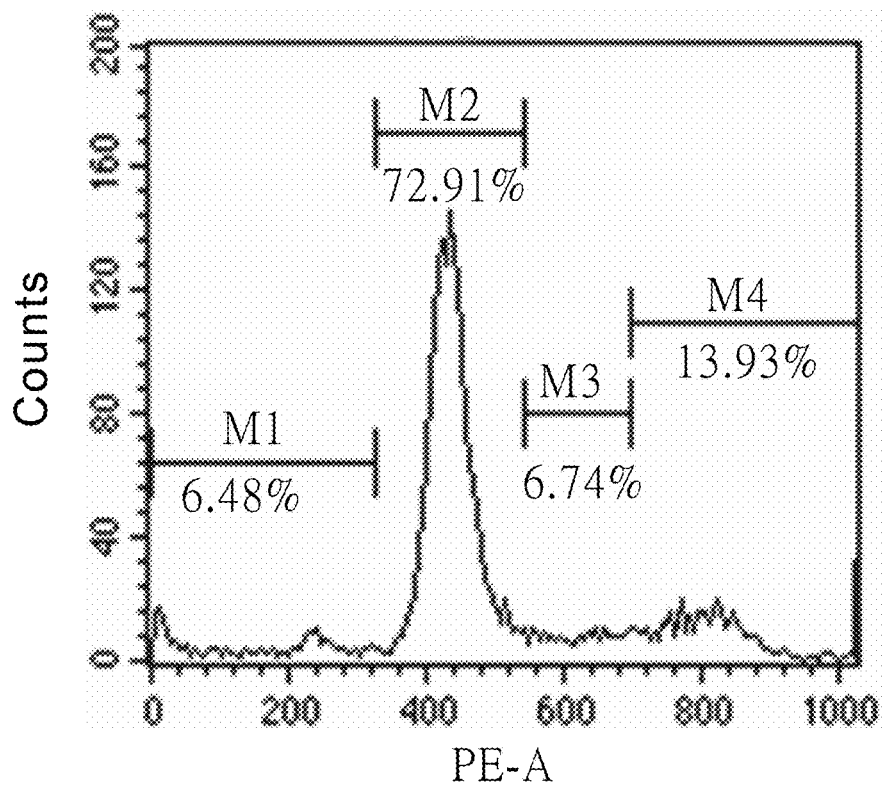
FIG. 18D shows the detection result of cell cycle of Hep3B cells after treatment with 6.25 µM Amlodipine.
Figure 18E:
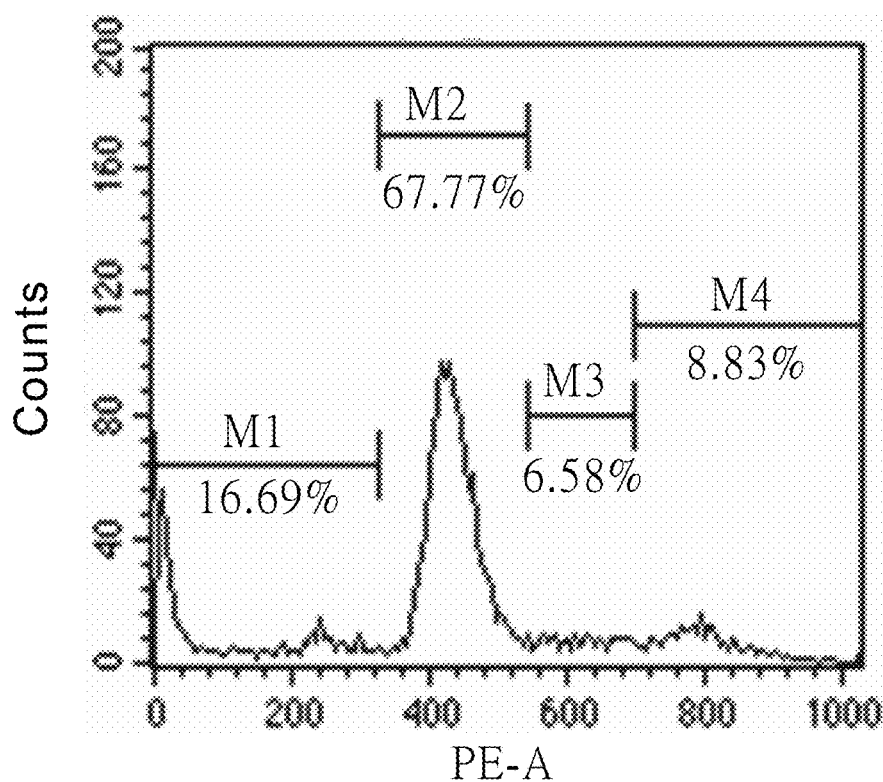
FIG. 18E shows the detection result of cell cycle of Hep3B cells after treatment with 12.5 µM Amlodipine.
Figure 18F:
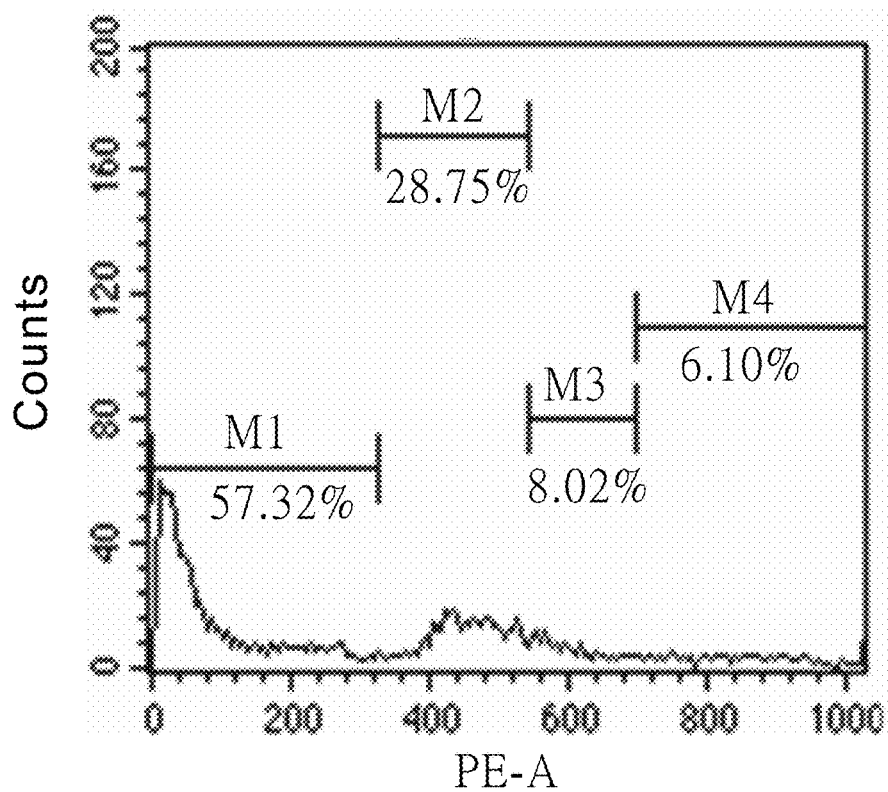
FIG. 18F shows the detection result of cell cycle of Hep3B cells after treatment with 25 µM Amlodipine.
Figure 19:
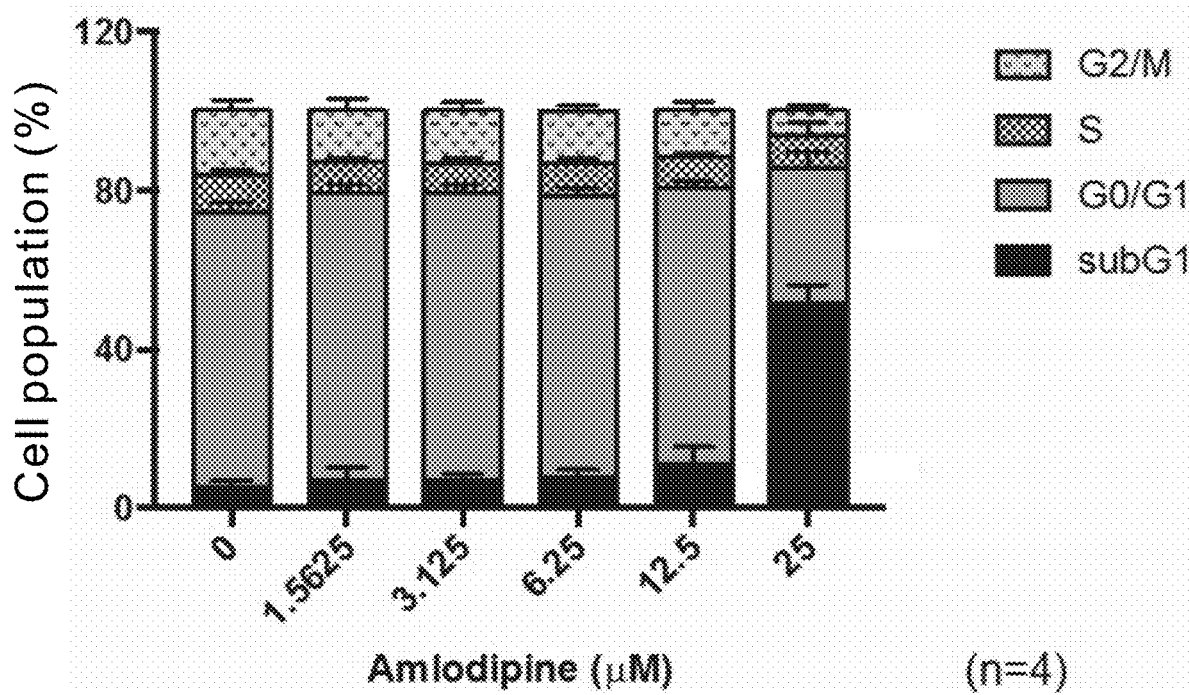
FIG. 19 shows the result of cell cycle by flow cytometry of Hep3B cells after treatment with various concentrations of Amlodipine.
Figure 20A:
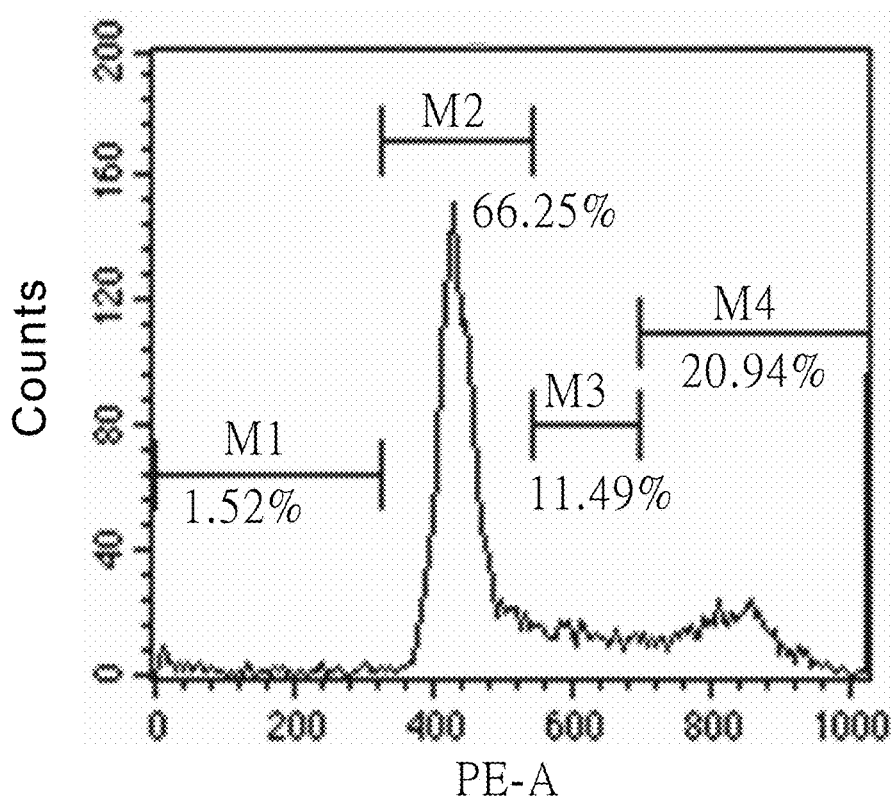
FIG. 20A shows the result of cell cycle by flow cytometry of HepG2 cells receiving no treatment with Amlodipine.
Figure 20B:
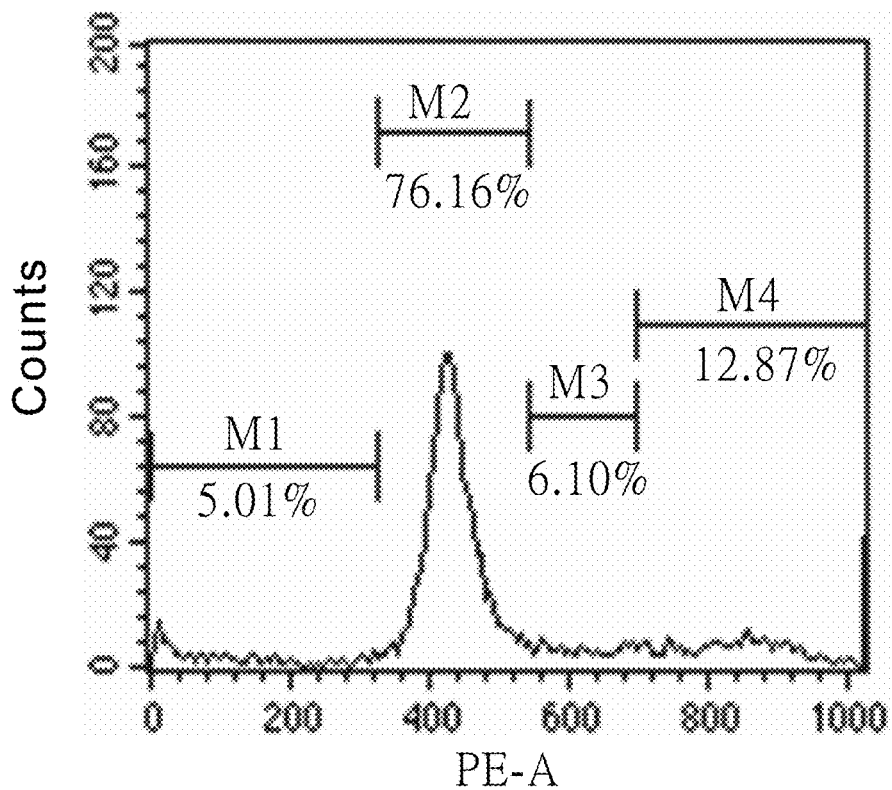
FIG. 20B shows the result of cell cycle by flow cytometry of HepG2 cells after treatment with 12.5 µM Amlodipine for 12 hrs.
Figure 20C:
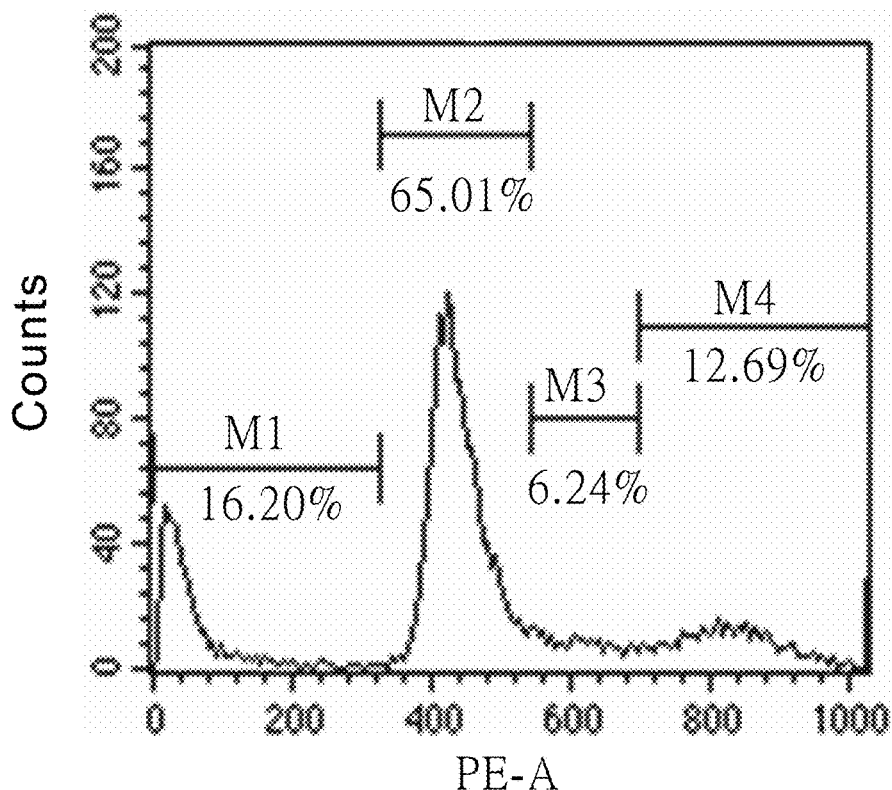
FIG. 20C shows the result of cell cycle by flow cytometry of HepG2 cells after treatment with 12.5 µM Amlodipine for 24 hrs.
Figure 20D:
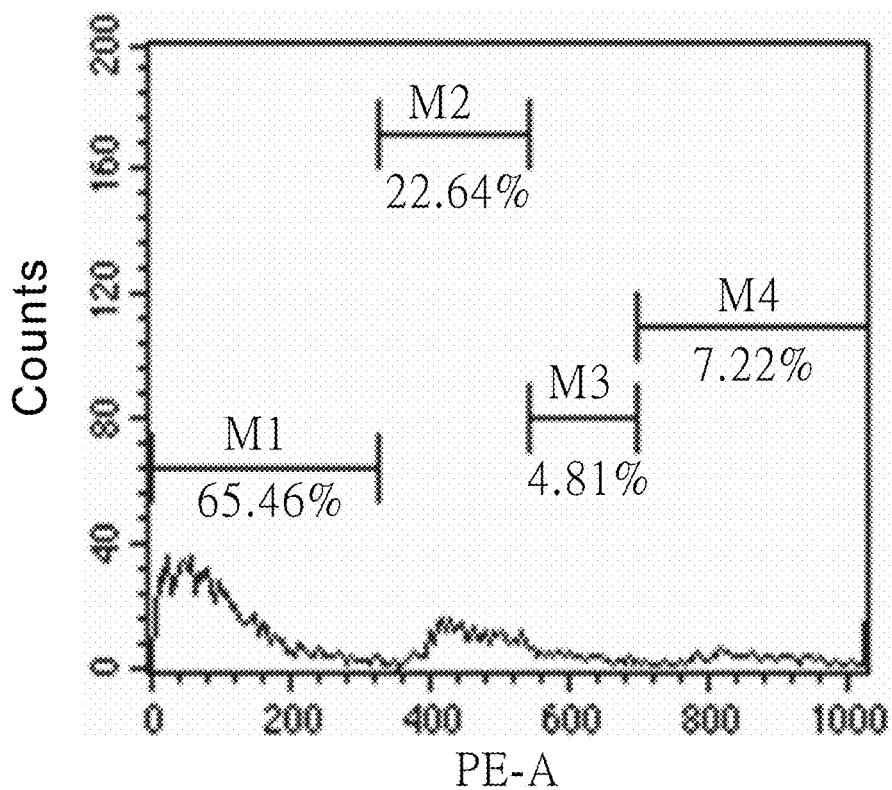
FIG. 20D shows the result of cell cycle by flow cytometry of HepG2 cells after treatment with 12.5 µM Amlodipine for 36 hrs.
Figure 20E:
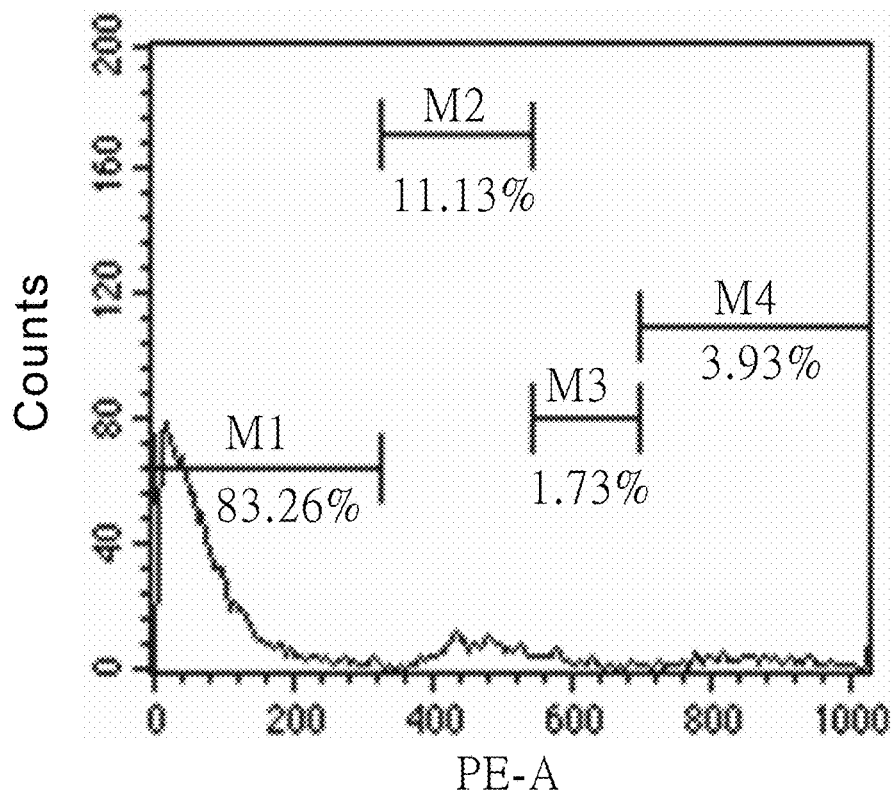
FIG. 20E shows the result of cell cycle by flow cytometry of HepG2 cells after treatment with 12.5 µM Amlodipine for 48 hrs.
Figure 21:
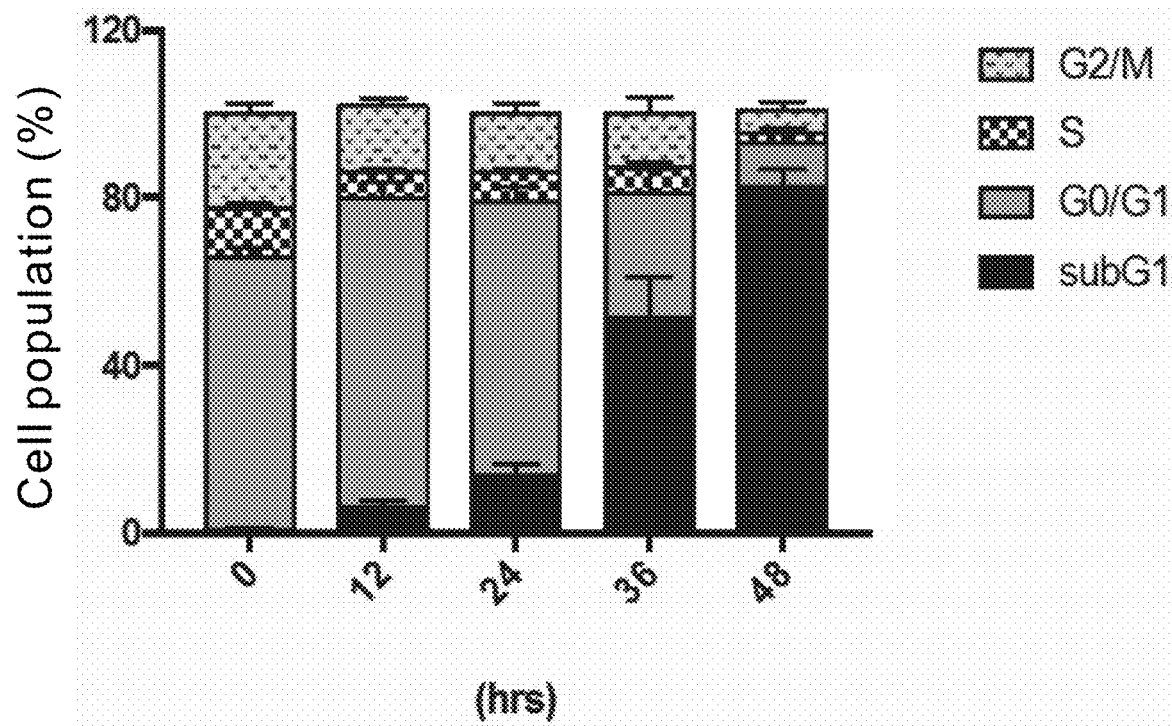
FIG. 21 shows the result of cell cycle by flow cytometry of HepG2 cells after treatment with Amlodipine for various times.
Figure 22A:
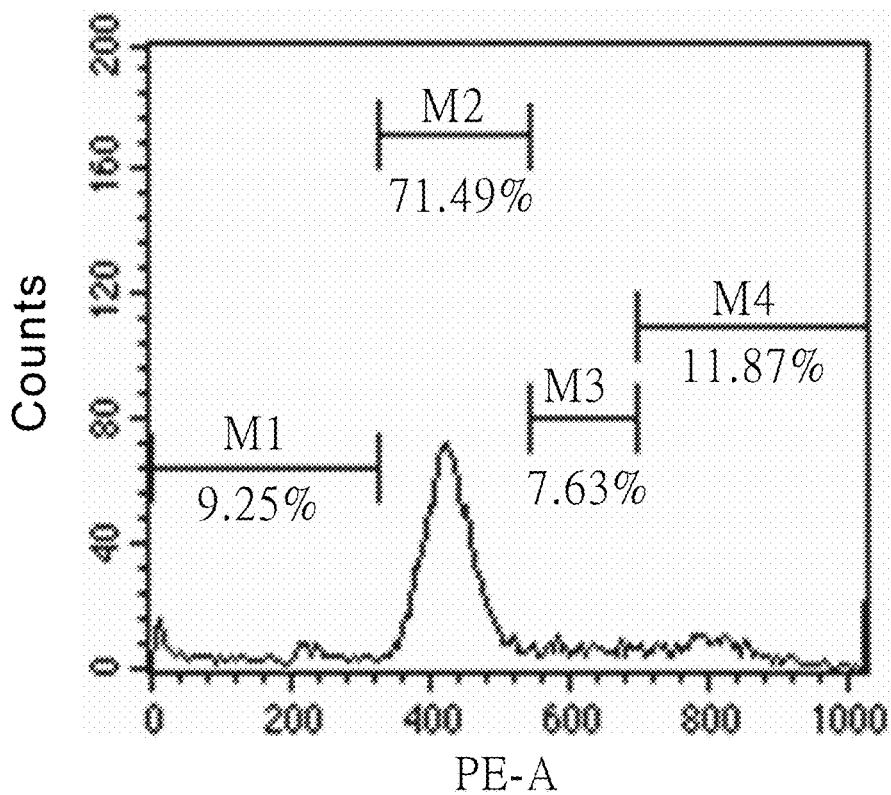
FIG. 22A shows the result of cell cycle by flow cytometry of Hep3B cells receiving no treatment with Amlodipine.
Figure 22B:
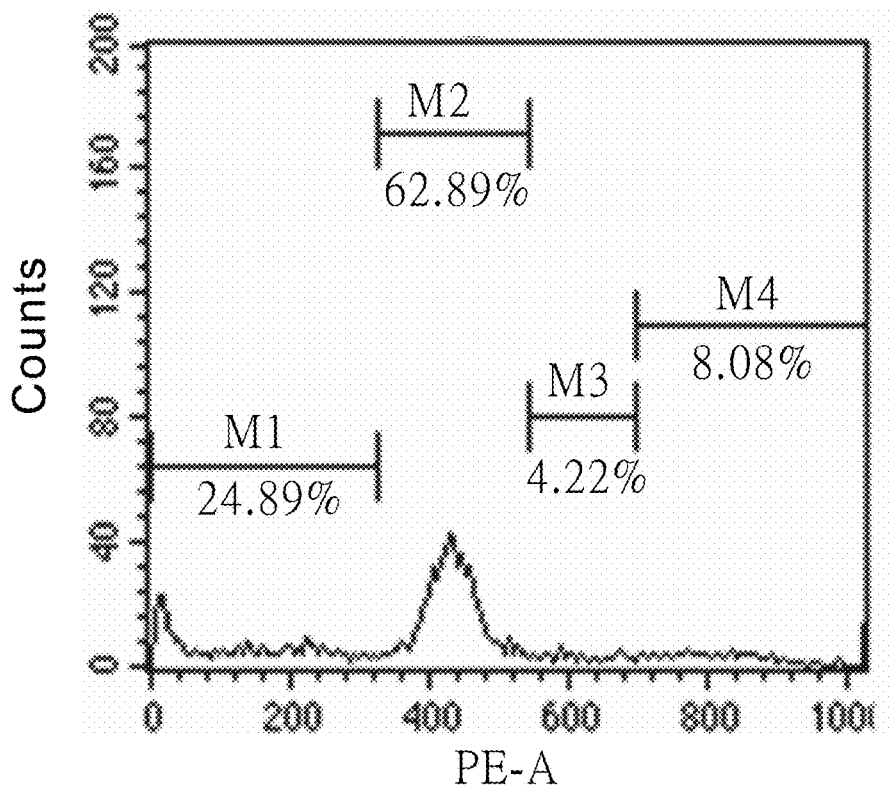
FIG. 22B shows the result of cell cycle by flow cytometry of Hep3B cells after treatment with 25 µM Amlodipine for 12 hrs.
Figure 22C:
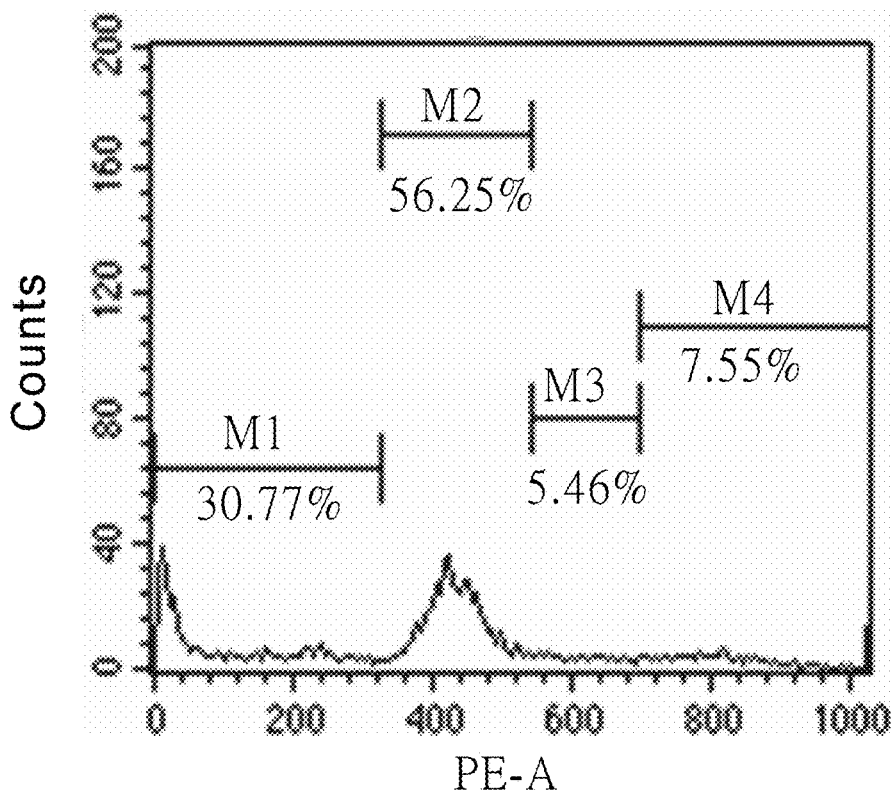
FIG. 22C shows the result of cell cycle by flow cytometry of Hep3B cells after treatment with 25 µM Amlodipine for 24 hrs.
Figure 22D:
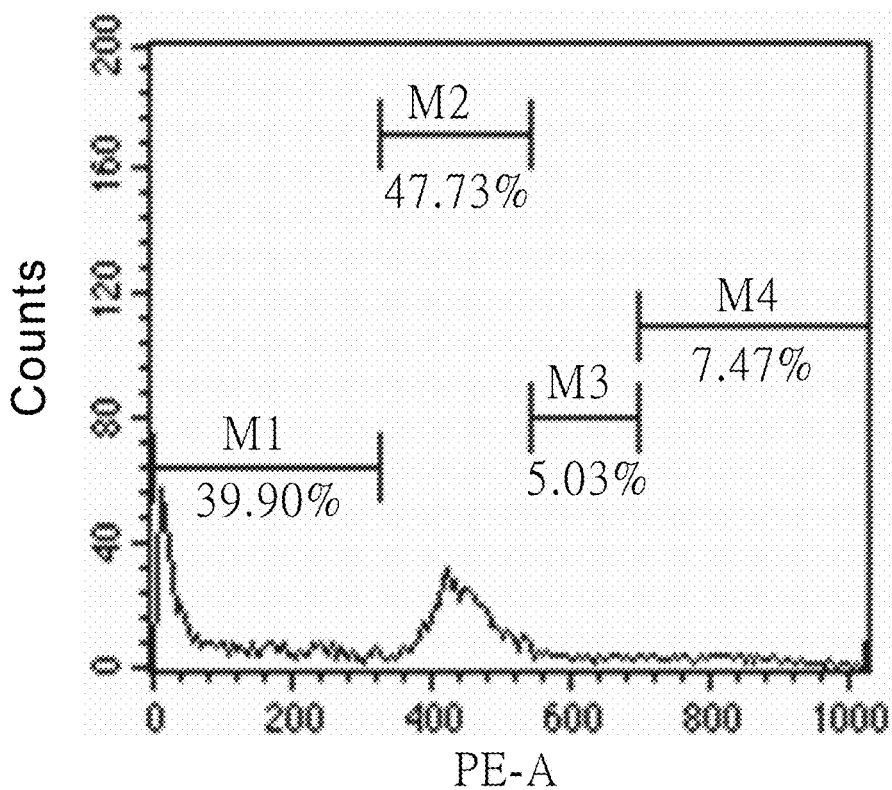
FIG. 22D shows the result of cell cycle by flow cytometry of Hep3B cells after treatment with 25 µM Amlodipine for 36 hrs.
Figure 22E:
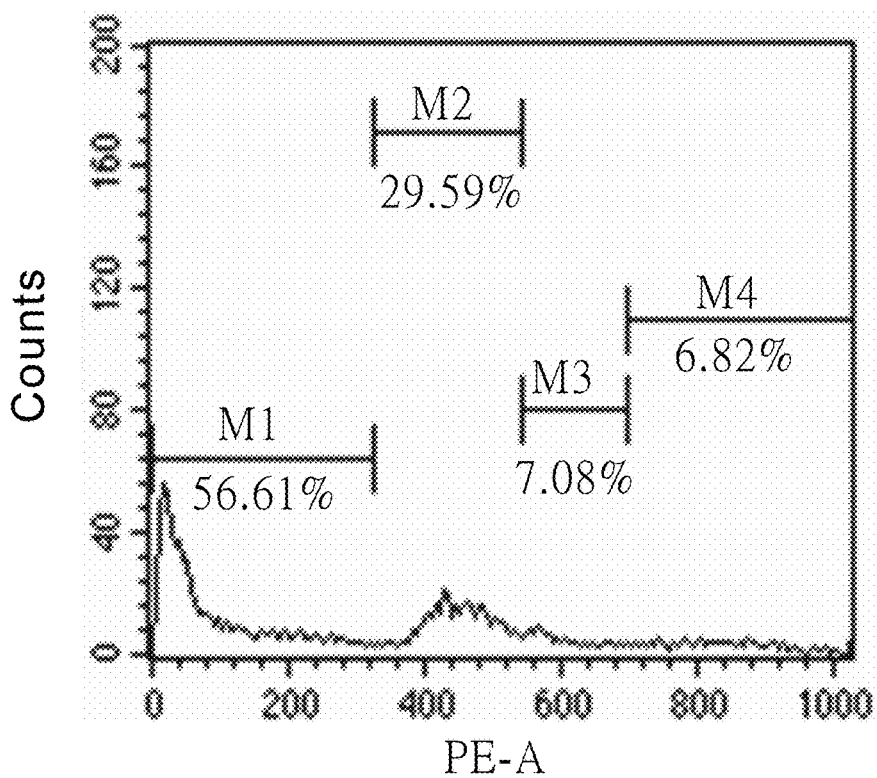
FIG. 22E shows the result of cell cycle by flow cytometry of Hep3B cells after treatment with 25 µM Amlodipine for 48 hrs.
Figure 23:
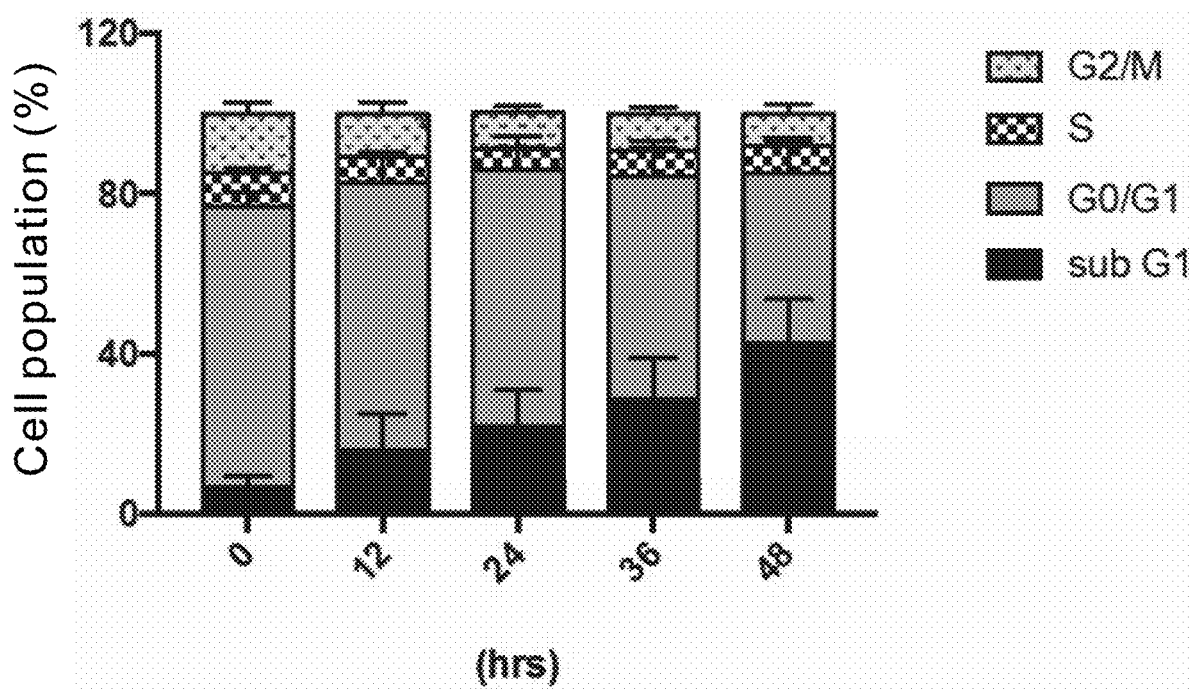
FIG. 23 shows the result of cell cycle by flow cytometry of Hep3B cells after treatment with Amlodipine for various times.
Figure 24:
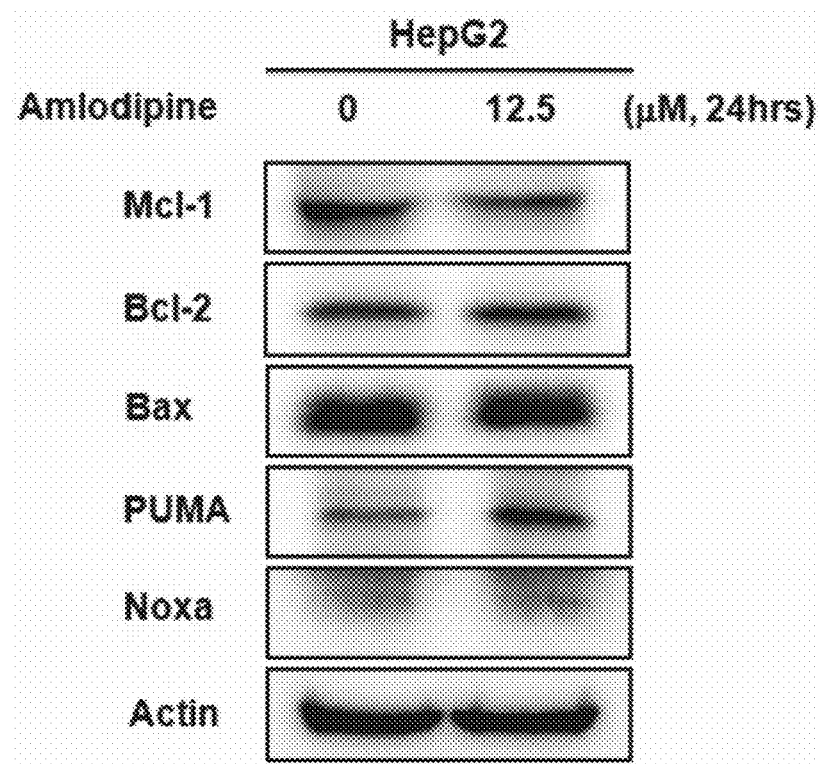
FIG. 24 shows the result (I) of protein expressions in HepG2 cells detected after treatment with various concentrations of Amlodipine.
Figure 25:
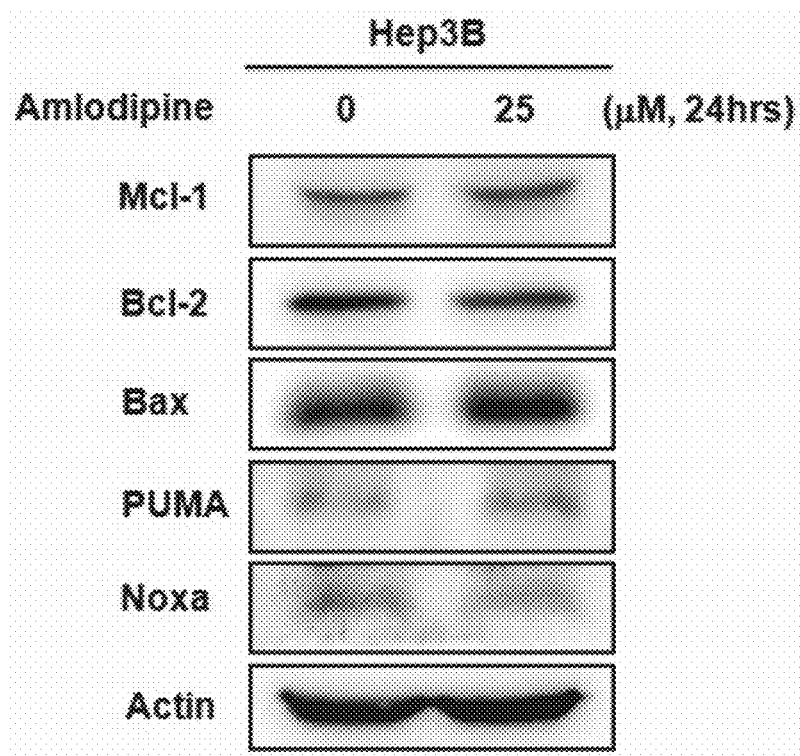
FIG. 25 shows the result (I) of protein expressions in Hep3B cells detected after treatment with various concentrations of Amlodipine.
Figure 26:
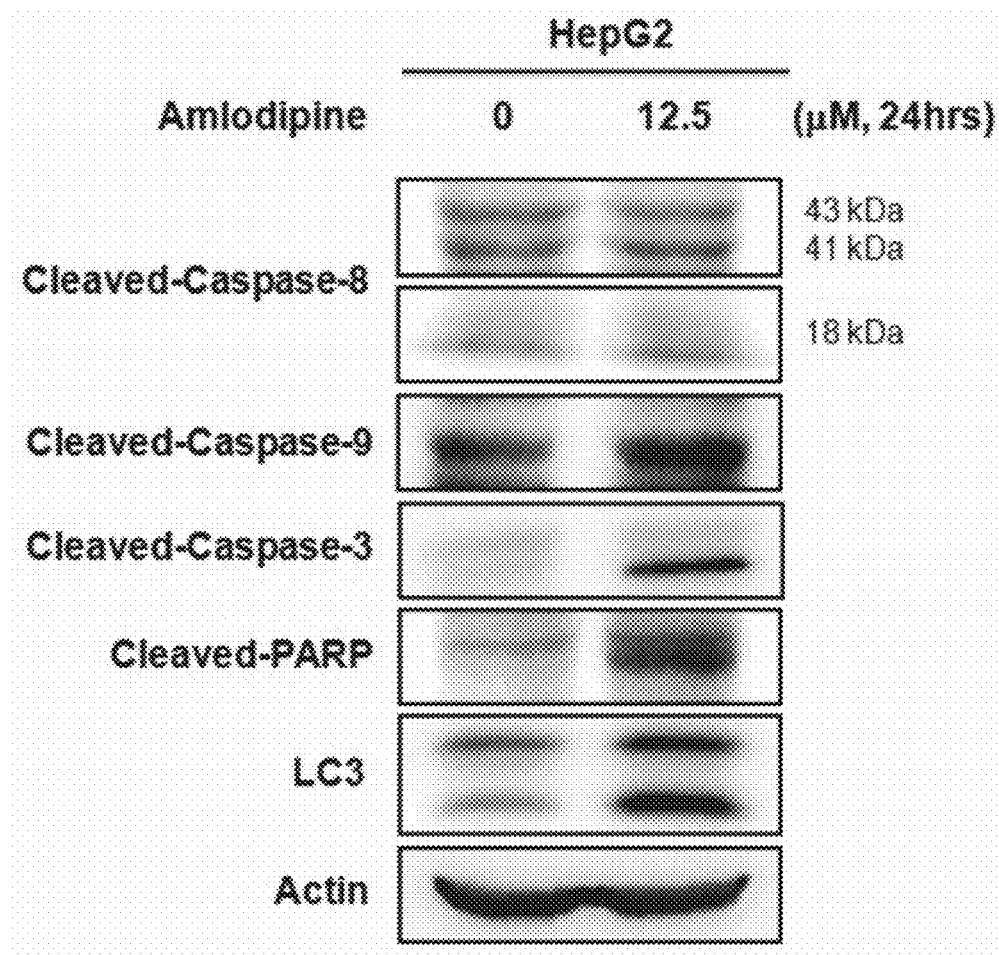
FIG. 26 shows the result (II) of protein expressions in HepG2 cells detected after treatment with various concentrations of Amlodipine.
Figure 27:
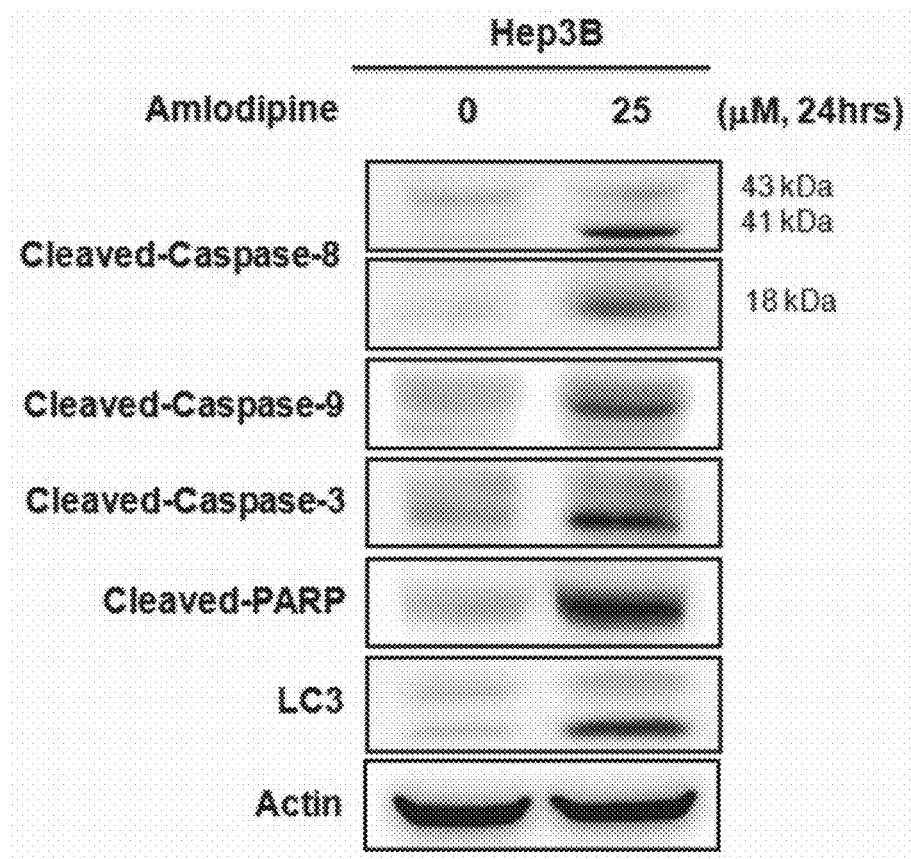
FIG. 27 shows the result (II) of protein expressions in Hep3B cells detected after treatment with various concentrations of Amlodipine.
Figure 28A:
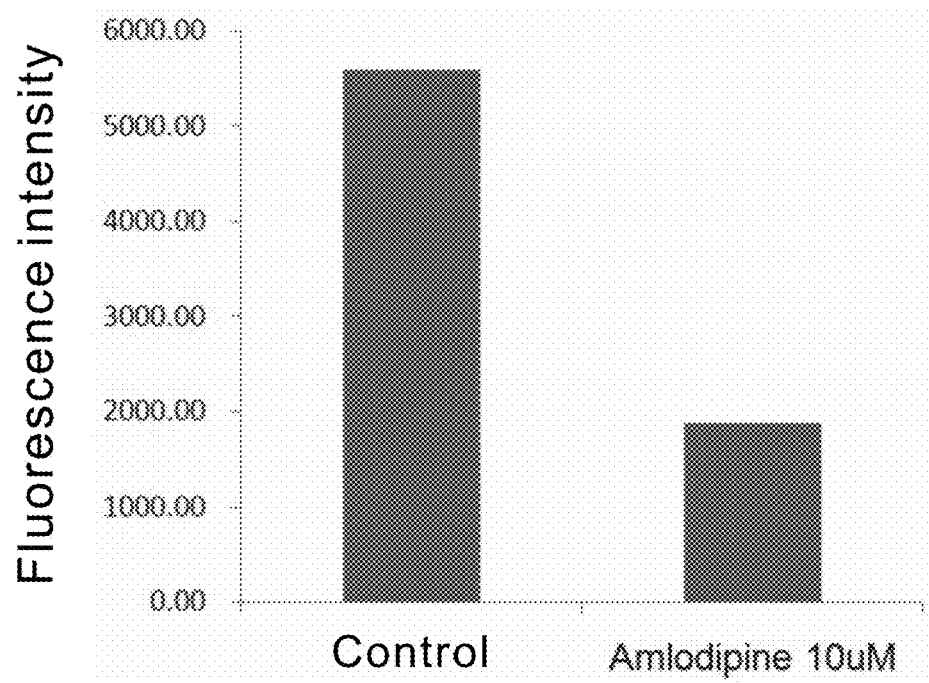
FIG. 28A shows the result of fluorescence intensity from HepG2 cells detected after treatment with various concentrations of Amlodipine for 48 hrs.
Figure 28B:
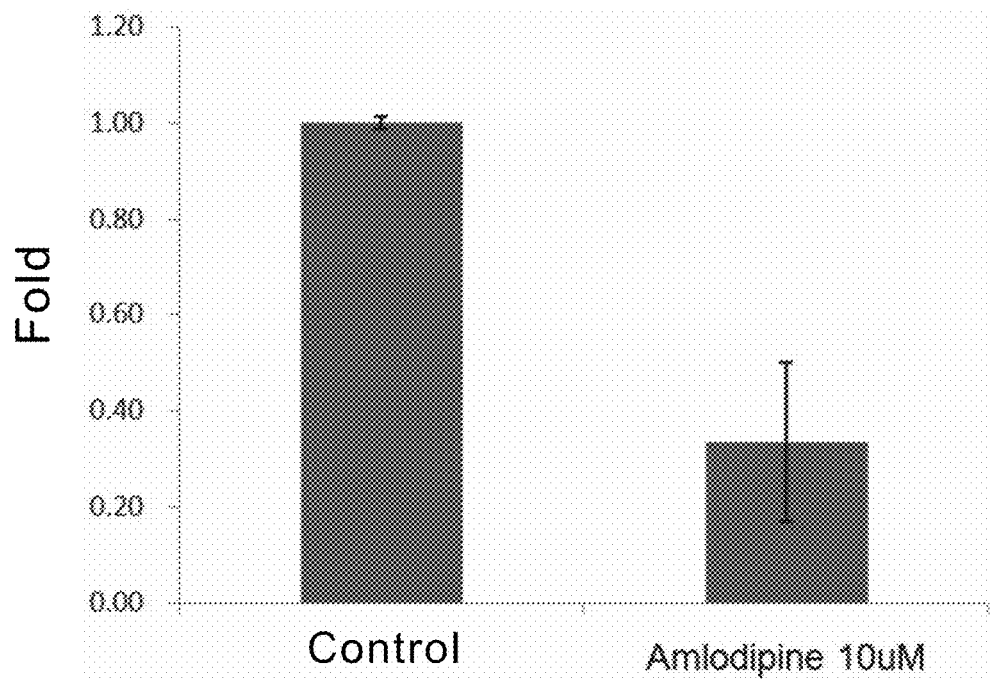
FIG. 28B shows the result of cell count of HepG2 cells detected after treatment with various concentrations of Amlodipine for 48 hrs.
Figure 29:
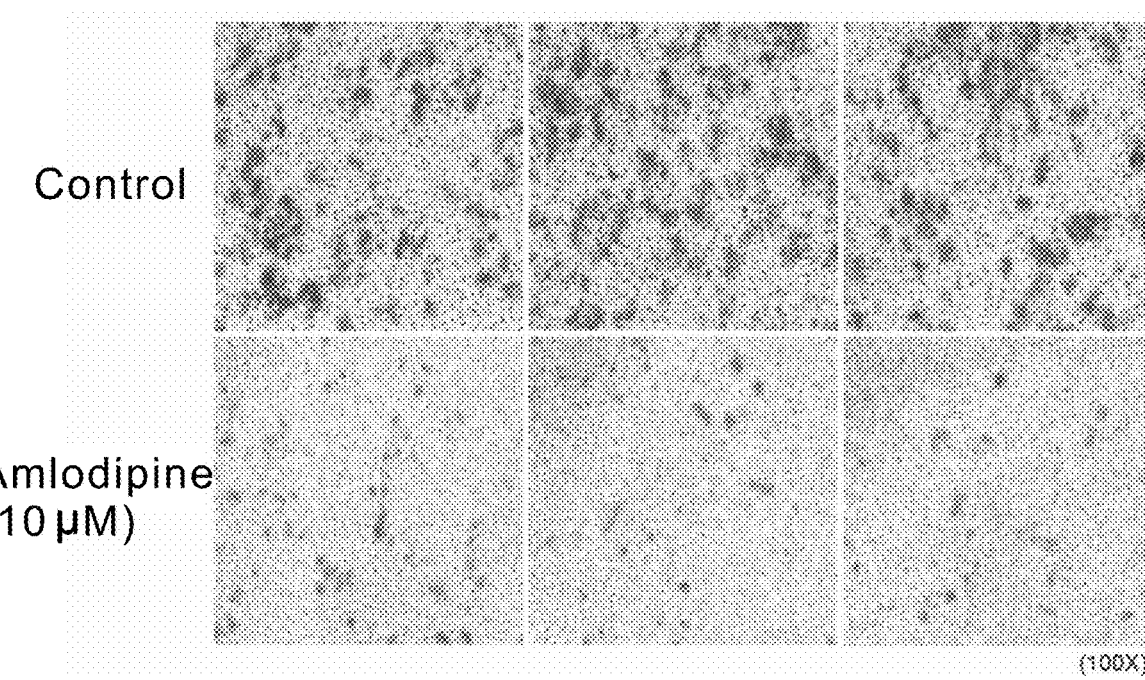
FIG. 29 shows the result of cell migration of HepG2 cells observed after treatment with various concentrations of Amlodipine for 48 hrs.
Figure 30A:
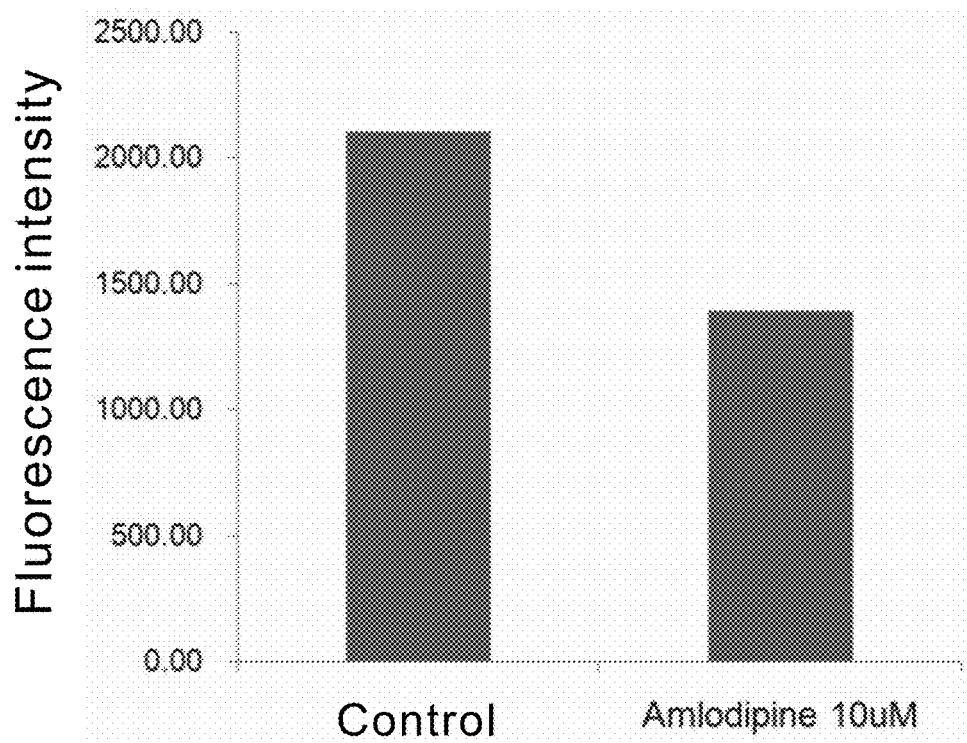
FIG. 30A shows the result of fluorescence intensity from Hep3B cells detected after treatment with various concentrations of Amlodipine for 72 hrs.
Figure 30B:
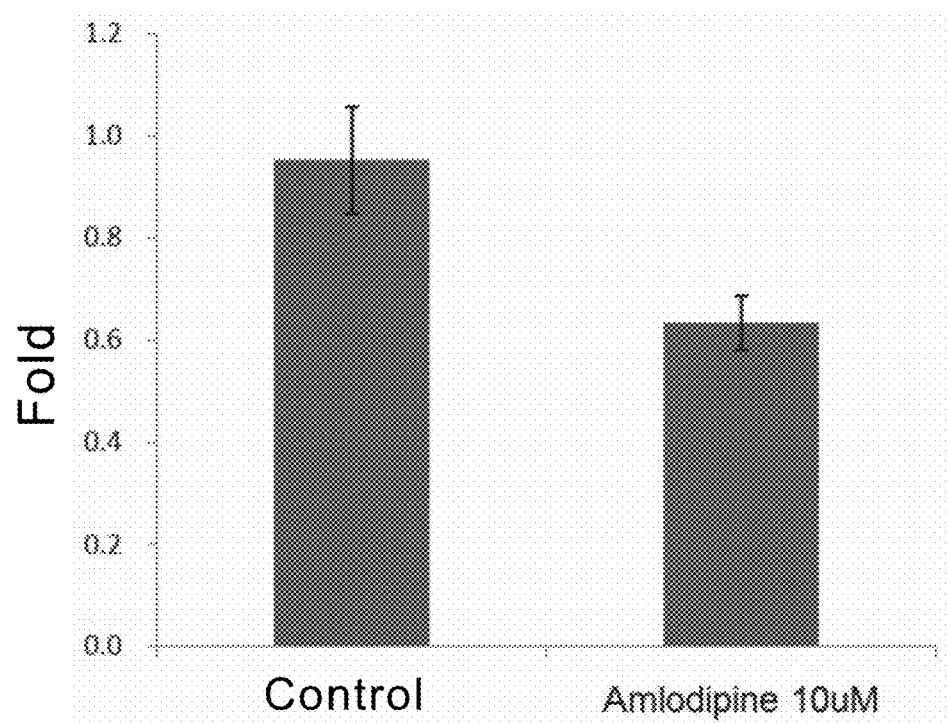
FIG. 30B shows the result of cell count of Hep3B cells detected after treatment with various concentrations of Amlodipine for 72 hrs.
Figure 31:
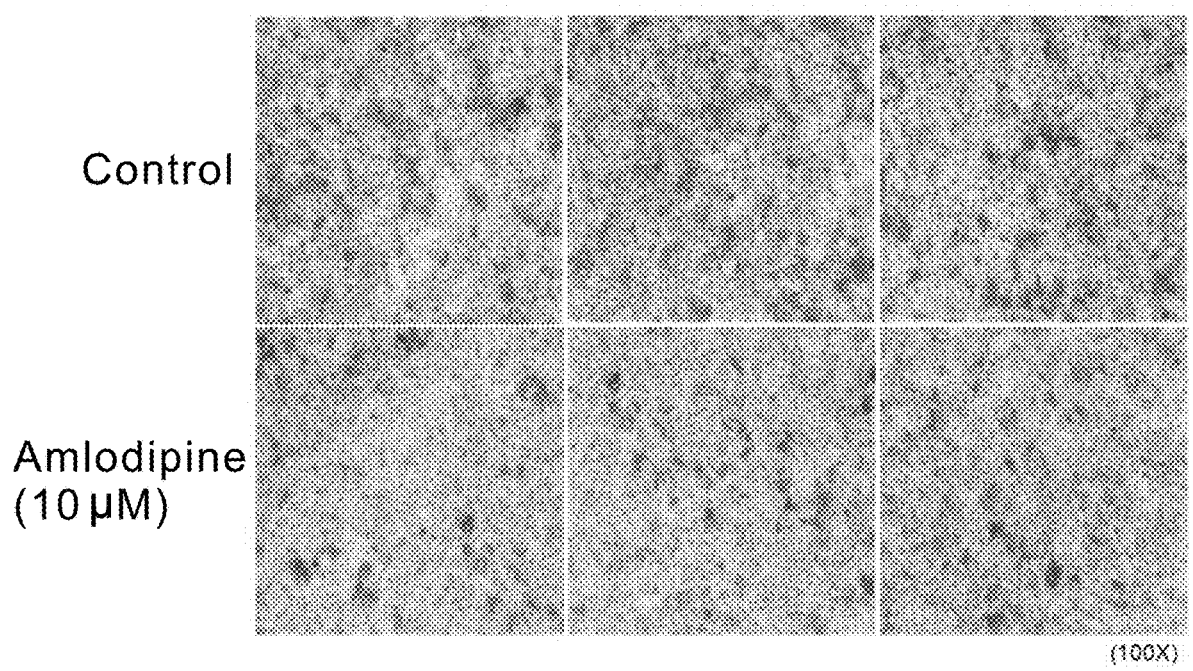
FIG. 31 shows the result of cell migration of Hep3B cells observed after treatment with various concentrations of Amlodipine for 72 hrs.

The HepG2 and Hep3B cells treated with various concentrations of Amlodipine for 72 hrs were added to WST-1 reagent. After 330 minutes of reaction, the absorbance at a wavelength of 420-480 nm was measured. The results are shown in FIGS. 9 and 10.

The HepG2 and Hep3B cells treated with various concentrations of Amlodipine for 48 hrs were scraped off with 0.05% Trypsin-EDTA, and then added to 2 mg/ml PI solution. The cell viability was analyzed by flow cytometry. The results are shown in FIGS. 11 to 15.

The results from FIGS. 9 to 15 show that the cell viability of liver cancer cells treated with Amlodipine is decreased, and as the concentration administered increases, the cell viability of liver cancer cells decreases accordingly. When the Amlodipine concentration is greater than or equal to 12.5 μM, the best inhibitory effect on the growth of liver cancer cells is achieved.

Example 5: Analysis of the Cell Cycle

The cell cycle of each liver cancer cell line treated under different conditions was analyzed by flow cytometry. The results are shown in FIGS. 16 to 23.

Referring to FIGS. 16 to 19, when each liver cancer cell line was treated with Amlodipine at a concentration of 12.5 μM or more for 48 hrs, most cells were unable to undergo cell division, specifically as shown in Tables 3 and 4 below.

TABLE 3

Cell cycle distribution of liver cancer cells HepG2 treated with various concentrations of Amlodipine for 48 hrs

| Amlodipine concentration | Proportion of cell distribution in cell cycle (%) | | | |
|---|---|---|---|---|
| (μM) | M1: | M2: | M3: | M4: |
| 0 | 1.95 | 68.79 | 10.58 | 18.84 |
| 1.5625 | 1.58 | 70.28 | 8.89 | 19.34 |
| 3.125 | 1.36 | 69.60 | 8.91 | 20.23 |
| 6.25 | 1.91 | 66.92 | 10.28 | 21.01 |
| 12.5 | 81.27 | 12.49 | 3.31 | 2.95 |
| 25 | 99.75 | 0.22 | 0.00 | 0.94 |

TABLE 4

Cell cycle distribution of liver cancer cells Hep3B treated with various concentrations of Amlodipine for 48 hrs

| Amlodipine concentration | Proportion of cell distribution in cell cycle (%) | | | |
|---|---|---|---|---|
| (μM) | M1: | M2: | M3: | M4: |
| 0 | 5.15 | 72.09 | 8.38 | 14.55 |
| 1.5625 | 5.34 | 74.88 | 7.06 | 12.82 |
| 3.125 | 6.51 | 73.83 | 6.63 | 13.17 |
| 6.25 | 6.48 | 72.91 | 6.74 | 13.93 |
| 12.5 | 16.96 | 67.77 | 6.58 | 8.83 |
| 25 | 57.32 | 28.75 | 8.02 | 6.10 |

Still further, each liver cancer cell line was treated with Amlodipine at a concentration of 12.5 μM for 0, 12, 24, 36 and 48 hrs, and the cell cycle was analyzed by flow cytometry. The results are shown in FIGS. 20 to 23. The proportion of cell distribution at each phase of the cell cycle is shown in Tables 5 and 6 below. The results show that as the time of treatment with Amlodipine increases, more liver cancer cells are inhibited from undergoing cell division.

TABLE 5

Cell cycle distribution of liver cancer cells HepG2 treated with Amlodipine for various times

| Treatment time (hr) | Proportion of cell distribution in cell cycle (%) | | | |
|---|---|---|---|---|
| | M1: | M2: | M3: | M4: |
| 0 | 1.52 | 66.25 | 11.49 | 20.94 |
| 12 | 5.01 | 76.16 | 6.10 | 12.87 |
| 24 | 16.20 | 65.01 | 6.24 | 12.69 |
| 36 | 65.46 | 22.64 | 4.81 | 7.22 |
| 48 | 83.26 | 11.13 | 1.73 | 3.93 |

TABLE 6

Cell cycle distribution of liver cancer cells Hep3B treated with Amlodipine for various times

| Treatment time (hr) | Proportion of cell distribution in cell cycle (%) | | | |
|---|---|---|---|---|
| | M1: | M2: | M3: | M4: |
| 0 | 9.25 | 71.49 | 7.63 | 11.87 |
| 12 | 24.89 | 62.89 | 4.22 | 8.08 |
| 24 | 30.77 | 56.25 | 5.46 | 7.55 |
| 36 | 39.90 | 47.73 | 5.03 | 7.47 |
| 48 | 56.61 | 29.59 | 7.08 | 6.82 |

Example 6: Protein Expression

The expression of apoptosis-related genes in each liver cancer cell line treated with various concentrations of Amlodipine for 24 hours were detected by Western blotting. The results are shown in FIGS. 24 to 27.

From the results shown in FIGS. 24 to 27, it can be seen that treatment of the liver cancer cells with Amlodipine results in the intracellular expression of apoptotic proteins, indicating that Amlodipine promotes apoptosis and is effective in treating cancers.

Example 7: Cell Metastasis

The HepG2 and Hep3B cells were separately cultured in an insert of the Transwell plate, then added with 10 μM Amlodipine and cultured for 48 or 72 hrs. The insert was placed in a serum-free DMEM medium containing 8 mM Calcien AM. Fluorescent staining was carried out in a culture environment at 37° C. After about 45-60 min, the cells were scraped off with 0.05% Trypsin-EDTA, and the fluorescence intensity at a wavelength of 490 to 520 nm was measured. The results are shown in FIGS. 28 to 31.

From the results of this example, the status of cancer cell metastasis gets known. In other words, the fluorescence intensity from the liver cancer cells treated with Amlodipine is lower than that from the liver cancer cells not treated with Amlodipine, thus indicating that Amlodipine can improve the status of cancer metastasis.

Example 8: Cell Invasion

Figure 32A:
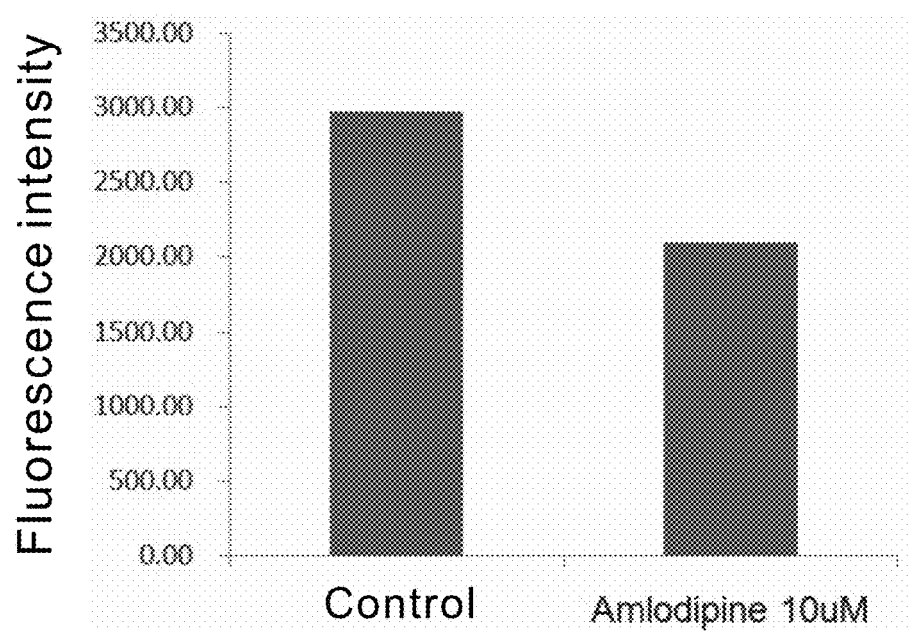
FIG. 32A shows the result of fluorescence intensity from HepG2 cells detected after treatment with various concentrations of Amlodipine for 72 hrs.
Figure 32B:
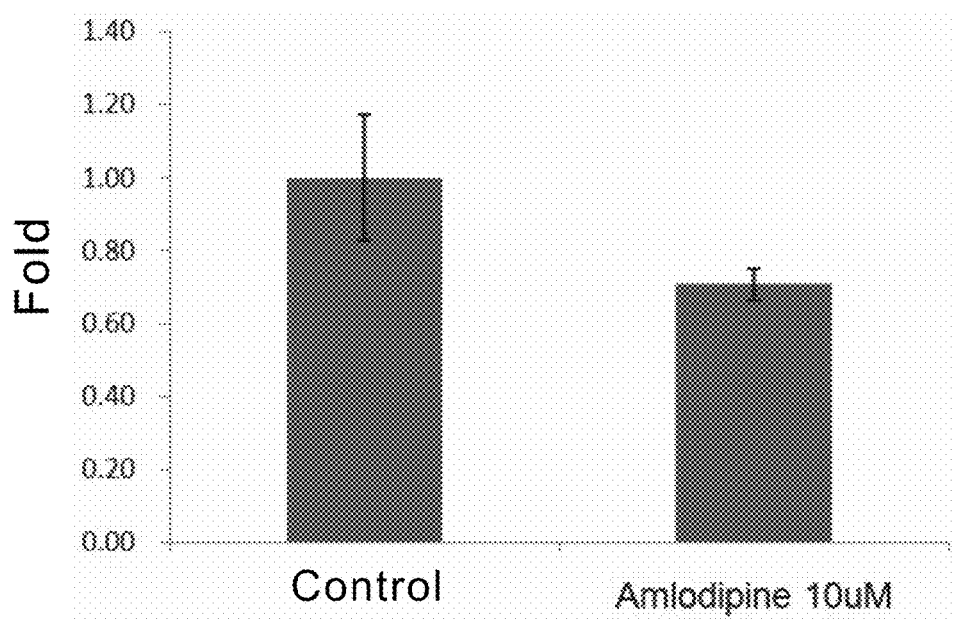
FIG. 32B shows the result of cell count of HepG2 cells detected after treatment with various concentrations of Amlodipine for 72 hrs.
Figure 33:
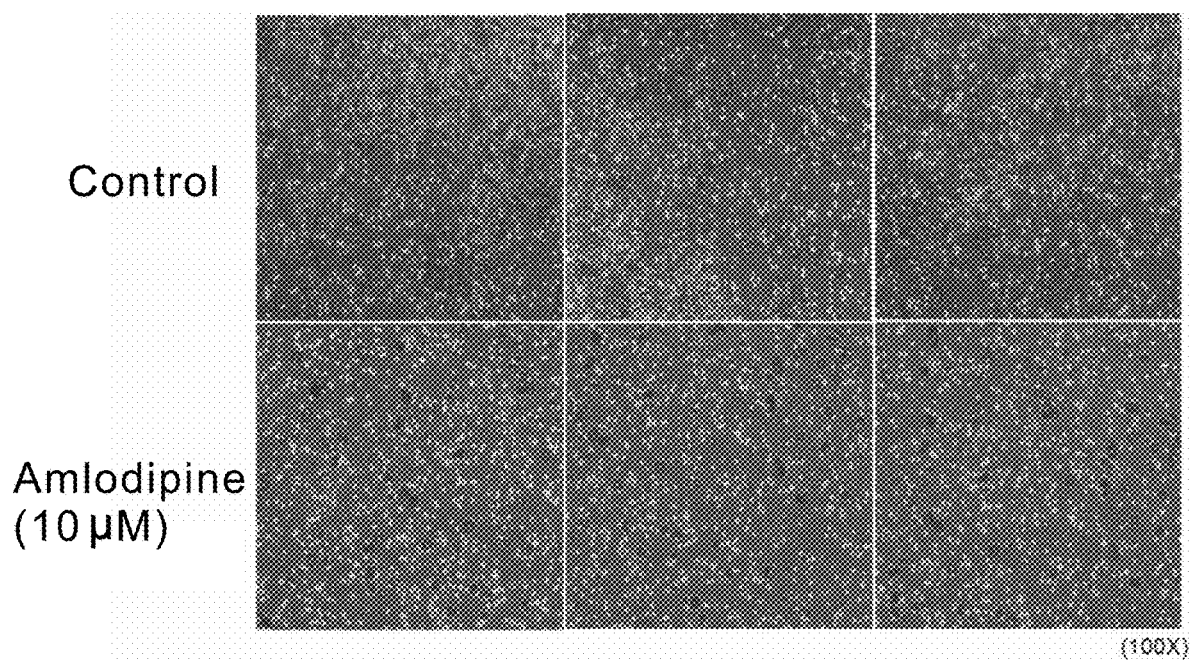
FIG. 33 shows the result of cell migration of HepG2 cells observed after treatment with various concentrations of Amlodipine for 72 hrs.

The HepG2 and Hep3B cells were separately cultured in the insert of the Transwell plate, then added with 10 μM Amlodipine and cultured for 48 or 72 hrs. The cells on the inner surface of the insert were taken out, and the insert was placed in methanol and stained with a crystal violet solution. The results photographed under a microscope are shown in FIGS. 32 and 33. From the results, it is found that the fluorescence intensity from the liver cancer cells treated with Amlodipine for 72 hrs is lower than that from the liver cancer cells not treated with Amlodipine. That is, Amlodipine is effective in slowing the progression of cancers, thereby achieving a therapeutic effect in the treatment of cancers.

It can be seen from the above embodiments and examples that the dihydropyridine calcium antagonist disclosed in the present invention has the effect of inhibiting the division and promoting the apoptosis of cancer cells, that is, the dihydropyridine calcium antagonist disclosed in the present invention is useful in a pharmaceutical composition for treating cancers. Furthermore, as the dose of the dihydropyridine calcium antagonist administered is increased or as the duration of administration is increased, the effect of inhibiting the growth of cancer cells is better.

What is claimed is:

1. A method for treating a cancer with a dihydropyridine calcium antagonist, comprising administering an effective amount of a dihydropyridine calcium antagonist to a cancer patient, wherein the dihydropyridine calcium antagonist is used at a dosage from 100 mg/90 day to 120 mg/30 day,
    wherein the administration of the dihydropyridine calcium antagonist to the cancer patient is to inhibit cancer metastasis.
2. The method for treating a cancer with a dihydropyridine calcium antagonist according to claim 1, wherein the dihydropyridine calcium antagonist is Amlodipine.
3. The method for treating a cancer with a dihydropyridine calcium antagonist according to claim 2, wherein Amlodipine is used at an average dosage of 1 mg/day to 4 mg/day.
4. The method for treating a cancer with a dihydropyridine calcium antagonist according to claim 1, wherein the cancer is selected from the group consisting of gastric cancer, liver cancer, lung cancer, breast cancer, colorectal cancer, pancreatic cancer, bladder cancer, and cervical cancer.
5. The method for treating a cancer with a dihydropyridine calcium antagonist according to claim 1, wherein the cancer is advanced cancer.

* * * * *